US011660337B2

(12) United States Patent
Li et al.

(10) Patent No.: US 11,660,337 B2
(45) Date of Patent: May 30, 2023

(54) TRIPLE LIVE VACCINE OF CANINE DISTEMPER VIRUS, CANINE PARVOVIRUS AND CANINE INFECTIOUS HEPATITIS VIRUS

(71) Applicant: Liaoning Yikang Biological Corporation Limited, Liaoyang (CN)

(72) Inventors: Fengyan Li, Liaoyang (CN); Xiuwei Shu, Liaoyang (CN); Bo Wang, Liaoyang (CN); Yiping Wang, Liaoyang (CN); Wenyou Luo, Liaoyang (CN); Shenglei Chen, Liaoyang (CN); Yanxia Liu, Liaoyang (CN)

(73) Assignee: Liaoning Yikang Biological Corporation Limited, Liaoyang (CN)

( * ) Notice: Subject to any disclaimer, the term of this patent is extended or adjusted under 35 U.S.C. 154(b) by 0 days.

(21) Appl. No.: 17/502,116

(22) Filed: Oct. 15, 2021

(65) Prior Publication Data

US 2022/0118083 A1 Apr. 21, 2022

(30) Foreign Application Priority Data

Oct. 20, 2020 (CN) ......................... 202011128453.4

(51) Int. Cl.

| | |
|---|---|
| ***A61K 39/29*** | (2006.01) |
| ***A61K 39/23*** | (2006.01) |
| ***A61K 39/175*** | (2006.01) |
| ***A61K 39/00*** | (2006.01) |

(52) U.S. Cl.

CPC ............ *A61K 39/29* (2013.01); *A61K 39/175* (2013.01); *A61K 39/23* (2013.01); *A61K 2039/552* (2013.01); *C12N 2710/10334* (2013.01); *C12N 2750/14034* (2013.01); *C12N 2760/18434* (2013.01)

(58) Field of Classification Search

CPC ...... A61K 39/29; A61K 39/175; A61K 39/23; A61K 2039/552; C12N 2710/10334; C12N 2750/14034; C12N 2760/18434

USPC ....................... 424/93.3, 213.1, 229.1, 233.1

See application file for complete search history.

(56) References Cited

U.S. PATENT DOCUMENTS

| | | | | | |
|---|---|---|---|---|---|
| 3,354,038 | A * | 11/1967 | Bass | A61K 39/175 | 435/237 |
| 5,047,238 | A * | 9/1991 | Acree | A61K 39/12 | 424/221.1 |

OTHER PUBLICATIONS

Badgett et al. (2002) J. Virol., vol. 76 (20), 10524-10529.*

"Veterinary Pharmacopoeia of the People's Republic of China", 2015 Edition, Published by China Agriculture Press, excepts, 21 pages.

* cited by examiner

*Primary Examiner* — Anne Marie S Wehbe

(74) *Attorney, Agent, or Firm* — RatnerPrestia

(57) ABSTRACT

The present invention discloses a combination of vaccine strains for treating, preventing, relieving or controlling Canine Distemper, Canine Parvovirus Enteritis and Canine Infectious Hepatitis, comprising: Canine Distemper virus vaccine strain with the microorganism deposition accession number CGMCC No. 19397, Canine Parvovirus vaccine strain with the microorganism deposition accession number CGMCC No. 19398 and Canine Infectious Hepatitis virus vaccine strain with the microorganism deposition accession number CGMCC No. 19396. The three vaccine strains of the combination of vaccine strains are low in toxicity and good in immunogenicity. The present invention further discloses a live vaccine composition using the above-mentioned combination of vaccine strains as immunogen. The vaccine composition is safe and effective.

11 Claims, 4 Drawing Sheets

Specification includes a Sequence Listing.

TRIPLE LIVE VACCINE OF CANINE DISTEMPER VIRUS, CANINE PARVOVIRUS AND CANINE INFECTIOUS HEPATITIS VIRUS

CROSS-REFERENCE TO RELATED APPLICATIONS

This application claims priority to Chinese Application No. 202011128453.4, filed Oct. 20, 2020, the content of which is incorporated herein by reference in its entirety for all purposes.

REFERENCE TO SEQUENCE LISTING

The present application is being filed along with a Sequence Listing in electronic format. The Sequence Listing is provided as a file entitled US17502116_Sequence listing.txt created on Apr. 10, 2023, which is 1,775 bytes in size. The sequences in the electronic format of the Sequence Listing are identical to those in Chinese Application No. 202011128453.4 and incorporated herein by reference in their entireties.

BACKGROUND

Field of Invention

The present invention belongs to the preventive veterinary field, and relates to a method for preparing multiple vaccines of Canine Distemper virus, Canine Parvovirus and Canine Infectious Hepatitis (also called Infectious Canine Hepatitis or Canine Viral Hepatitis) virus and the applications thereof.

Background of the Invention

Canine Distemper (CD) is an acute and highly contagious infectious disease caused by Canine Distemper virus (CDV) of Morbillivirus of Paramyxoviridae, which makes various animals such as Canidae, Mustelidae, Felidae and the like infection. This disease mainly injures the respiratory system, digestive system and nervous system of animals and has higher morbidity and lethality. Its naturally infected hosts have been continuously extended to various terrestrial and aquatic animals, and there also has potential zoonosis, which cause extensive concerns in zoological circles and medical circles.

Canine Parvovirus (CPV) is a pathogen that causes fulminating infectious disease to dogs, and the acute hemorrhagic enteritis and nonsuppurative myocarditis caused by Canine Parvovirus are the most severe acute and contagious infectious diseases that threaten and harm to the dog industry in the world at present. The disease has been spread to all kinds of dog groups all over the world, and CPV is widely spread in both wild and domesticated dog groups. With the substantial increase of the feeding amount of working dogs, laboratory dogs and pet dogs in China, Canine Parvovirus infection is increasingly serious, which brings great economic loss to dog industry, and becomes one of major epidemic diseases harm to dog industry.

In the discovered mammalian adenoviridaes, Canine Adenovirus (CAV) is an animal virus with the strongest pathogenicity and its morphological structure is studied more clearly. Its CAV-1 is the pathogen that causes Canine Infectious Hepatitis as well as bear and fox encephalitis; CAV-2 makes canine and fox develop infectious laryngotracheitis. CAV not only is prevalent in the domesticated canine and fox in China and around the world, but also is extensively prevalent in animals such as wild fox, bear, coyote, raccoon and the like. The mortality rate of the disease is up to 40%, and thus it causes huge economic loss to breeding industry. Studies indicate that the dogs immunized with CAV-2 can effectively produce the immunity to CAV-1 high virulence. Therefore, it has great significance to develop safe and effective vaccine of CAV-2 type. Canine Infectious Hepatitis mainly occurs in young dogs under one year old. Adult dogs rarely develop Canine Infectious Hepatitis and most of them are recessive infection. Even if getting sick, they can often endure it. Sick dogs and virus-carrying dogs are main sources of infection. Both secretions and excrements of sick dogs contain virus, and the recovered virus-carrying dogs, can discharge virus in the urine for a long time. The disease is mainly infected through digestive tract, and placental infection is also possible. Respiratory type cases can be infected through respiratory tract. Ectoparasites can be transmission medium.

At present, the vaccines extensively used in China are mainly single vaccine or multiple attenuated vaccines. They play positive role on preventing and controlling the major epidemic disease of dogs, however, there are also reports on the occurrence of major epidemic diseases some times. Except for the reasons of the interference of maternal antibodies and other viruses, vaccine titer, improper usage and the like, it is urgent to verify whether the epidemic situation is caused by the emergence of virus variants or not. Meanwhile, a majority of these currently used vaccines are the duplicates of foreign vaccines, the background of virus seeds species is unclear and the number of cell generations is relatively high, and it is difficult to guarantee both immunogenicity and safety. The Chinese patent application with the application number 201010244965.7 discloses a triple live vaccine of Canine Distemper, Canine Parvovirus and Canine Adenovirus type I and the preparation method thereof, but its virus challenge protection rate is not high, and it cannot provide good immune protection effectively against all virus strains. Therefore, it is extremely urgent to develop a vaccine suitable for Chinese epidemic strains.

SUMMARY

Compared with the traditional single vaccine immunizations, the triple live vaccine to Canine Distemper, Canine Parvovirus Enteritis and Canine Infectious Hepatitis (D2 strain+P6 strain+A22 strain) prepared in the present invention reduces the number of immunizations, prevents animals from stress responses caused by fixation, reaches the purpose of preventing multiple diseases with one vaccination, and increases production efficiency.

In order to solve the problems exist in the prior art, in the first aspect, the present invention provides a combination of vaccine strains for preventing Canine Distemper, Canine Parvovirus Enteritis and Canine Infectious Hepatitis, or a combination of vaccine strains for preventing Canine Distemper and Canine Parvovirus Enteritis, or a combination of vaccine strains for preventing Canine Parvovirus Enteritis and Canine Infectious Hepatitis.

The vaccine strains comprise Canine Distemper virus vaccine strain, Canine Parvovirus vaccine strain and Canine Infectious Hepatitis virus vaccine strain, or the vaccine strains comprise Canine Distemper virus vaccine strain and Canine Parvovirus vaccine strain, or the vaccine strains comprise Canine Parvovirus vaccine strain and Canine Infectious Hepatitis virus vaccine strain.

The Canine Distemper virus vaccine strain is the viral strain with the microorganism deposition accession number CGMCC No. 19397.

The Canine Parvovirus vaccine strain is the viral strain with the microorganism deposition accession number CGMCC No. 19398.

The Canine Infectious Hepatitis virus vaccine strain is the viral strain with the microorganism deposition accession number CGMCC No. 19396.

In the second aspect, the present invention provides a vaccine composition for preventing Canine Distemper, Canine Parvovirus Enteritis and Canine Infectious Hepatitis, or a vaccine composition for preventing Canine Distemper and Canine Parvovirus Enteritis, or a vaccine composition for preventing Canine Parvovirus Enteritis and Canine Infectious Hepatitis, wherein the vaccine composition uses the combination of vaccine strains of the first aspect of the present invention as immunogen.

In some embodiments, the raw materials of the vaccine composition comprise the immunogen and excipients.

In some embodiments, the vaccine composition is a live vaccine composition.

In some embodiments, in the vaccine compositions, the ratio of the dosage of the Canine Parvovirus vaccine strains, the dosage of the Canine Infectious Hepatitis virus vaccine strains and the dry weight dosage of the excipients is 0.5-3×$10^{5.0}$ $TCID_{50}$: 0.5-3×$10^{5.0}$$TCID_{50}$: 200-400 mg (such as 1.0×$10^{5.0}$$TCID_{50}$, 1.5×$10^{5.0}$$TCID_{50}$, 2.0×$10^{5.0}$ $TCID_{50}$, or 2.5×$10^{5.0}$$TCID_{50}$: 1.0×$10^{5.0}$$TCID_{50}$, 1.5×$10^{5.0}$ $TCID_{50}$, 2.0×$10^{5.0}$ $TCID_{50}$, or 2.5×$10^{5.0}$$TCID_{50}$: 220 mg, 240 mg, 260 mg, 280 mg, 300 mg, 320 mg, 340 mg, 360 mg, or 380 mg), preferably, 1×$10^{5.0}$ $TCID_{50}$: 1×$10^{5.0}$$TCID_{50}$: 315 mg.

In some embodiments, in the vaccine compositions, the ratio of the dosage of the Canine Distemper virus vaccine strains, the dosage of the Canine Infectious Hepatitis virus vaccine strains and the dry weight dosage of the excipients is 2-8×$10^{4.0}$$TCID_{50}$: 0.5-3×$10^{5.0}$$TCID_{50}$: 200-400 mg (such as, 3.0×$10^{4.0}$$TCID_{50}$/ml, 4.0×$10^{4.0}$ $TCID_{50}$/ml, 5.0×$10^{4.0}$ $TCID_{50}$/ml, 6.0×$10^{4.0}$ $TCID_{50}$/ml, or 7.0×$10^{4.0}$ $TCID_{50}$/ml: 1.0×$10^{5.0}$$TCID_{50}$, 1.5×$10^{5.0}$$TCID_{50}$, 2.0×$10^{5.0}$$TCID_{50}$, or 2.5×$10^{5.0}$$TCID_{50}$: 220 mg, 240 mg, 260 mg, 280 mg, 300 mg, 320 mg, 340 mg, 360 mg, or 380 mg), preferably, 5×$10^{4.0}$$TCID_{50}$: 1×$10^{5.0}$$TCID_{50}$: 315 mg.

In some embodiments, in the vaccine compositions, the ratio of the dosage of the Canine Distemper virus vaccine strains, the dosage of the Canine Parvovirus vaccine strains and the dry weight dosage of the excipients is 2-8×$10^{4.0}$ $TCID_{50}$: 0.5-3×$10^{5.0}$$TCID_{50}$: 200-400 mg (such as, 3.0×$10^{4.0}$$TCID_{50}$/ml, 4.0×$10^{4.0}$$TCID_{50}$/ml, 5.0×$10^{4.0}$$TCID_{50}$/ml, 6.0×$10^{4.0}$$TCID_{50}$/ml, or 7.0×$10^{4.0}$$TCID_{50}$/ml: 1.0×$10^{5.0}$$TCID_{50}$, 1.5×$10^{5.0}$$TCID_{50}$, 2.0×$10^{5.0}$$TCID_{50}$, or 2.5×$10^{5.0}$$TCID_{50}$: 220 mg, 240 mg, 260 mg, 280 mg, 300 mg, 320 mg, 340 mg, 360 mg, or 380 mg), preferably, 5×$10^{4.0}$ $TCID_{50}$: 1×$10^{5.0}$$TCID_{50}$: 315 mg.

In some embodiments, in the vaccine compositions, the ratio of the dosage of the Canine Distemper virus vaccine strains, the dosage of Canine Parvovirus vaccine strains, the dosage of the Canine Infectious Hepatitis virus vaccine strains and the dry weight dosage of the excipients is 2-8×$10^{4.0}$$TCID_{50}$: 0.5-3×$10^{5.0}$$TCID_{50}$: 0.5-3×$10^{5.0}$ $TCID_{50}$: 200-400 mg (such as, 3.0×$10^{40}$$TCID_{50}$/ml, 4.0×$10^{4.0}$$TCID_{50}$/ml, 5.0×$10^{4.0}$ $TCID_{50}$/ml, 6.0×$10^{4.0}$$TCID_{50}$/ml, or 7.0×$10^{4.0}$$TCID_{50}$/ml: 1.0×$10^{5.0}$$TCID_{50}$, 1.5×$10^{5.0}$ $TCID_{50}$, 2.0×$10^{5.0}$ $TCID_{50}$, 2.5×$10^{5.0}$ $TCID_{50}$: 1.0×$10^{5.0}$ $TCID_{50}$, 1.5×$10^{5.0}$ $TCID_{50}$, 2.0×$10^{5.0}$ $TCID_{50}$, or 2.5×$10^{5.0}$$TCID_{50}$: 220 mg, 240 mg, 260 mg, 280 mg, 300 mg, 320 mg, 340 mg, 360 mg, or 380 mg), preferably, 5×$10^{4.0}$$TCID_{50}$: 1×$10^{5.0}$$TCID_{50}$: 1×$10^{5.0}$$TCID_{50}$: 315 mg.

In some embodiments, the $TCID_{50}$ of the Canine Distemper virus vaccine strain is obtained by calculating according to Reed-Muench method on the basis of Vero cell culture.

In some embodiments, the $TCID_{50}$ of the Canine Parvovirus vaccine strain is obtained by calculating according to Reed-Muench method on the basis of F81 cell culture.

In some embodiments, the $TCID_{50}$ of the Canine Infectious Hepatitis virus vaccine strain is obtained by calculating according to Reed-Muench method on the basis of MDCK cell culture.

In some embodiments, the excipient is freeze-drying protectant.

In some embodiments, the freeze-drying protectant is the aqueous solution comprising 2-3 mg/mL (such as, 2.2 mg/mL, 2.4 mg/mL, 2.6 mg/mL, 2.8 mg/mL) polyvinyl pyrrolidone, 8-12 mg/mL (such as, 8.5 mg/mL, 9.0 mg/mL, 9.5 mg/mL, 10.0 mg/mL, 10.5 mg/mL, 11.0 mg/mL, and 11.5 mg/mL) sorbitol, 3-7 mg/mL (such as, 4.0 mg/mL, 5.0 mg/mL, and 6.0 mg/mL) glycine, 30-50 mg/mL (such as, 35 mg/mL, 40 mg/mL, and 45 mg/mL) sucrose, and 30-60 mg/mL (such as, 35 mg/mL, 40 mg/mL, 45 mg/mL, 50 mg/mL and 55 mg/mL) trehalose.

In the third aspect, the present invention provides the preparation method of the vaccine compositions of the second aspect of the present invention, and the preparation method comprises the following step:

preparing the vaccine compositions from the combinations of vaccine strains.

In some embodiments, the culture method of the vaccine strains comprises the following steps:

(i) respectively inoculating the vaccine strains in the combination of vaccine strains into culture cells to culture, to harvest the crude viral liquids of the vaccine strains; specific to the Canine Distemper virus vaccine strain, the culture cell is Vero cell; specific to the Canine Parvovirus vaccine strain, the culture cell is F81 cell; and specific to the Canine Infectious Hepatitis virus vaccine strain, the culture cell is MDCK cell; and (ii) purifying the crude viral liquids of the vaccine strains, to obtain purified viral liquids of vaccine strains.

In some embodiments, in step (i), when CPE reaches more than 80% (such as, 85%, 88%, 92%, 95%, and 98%), harvesting the crude viral liquids of the vaccine strains.

In some embodiments, in step (i), when CPE reaches more than 90%, harvesting the crude viral liquids of the vaccine strains.

In some embodiments, in step (i), inoculating in the dosage of MOI=0.005-0.01 (such as, 0.006, 0.007, 0.008, and 0.009).

In some embodiments, in step (i), specific to the Canine Distemper virus vaccine strain, inoculating in the dosage ratio of $10^{4.0}$$TCID_{50}$: 15-30 ml (such as, $10^{4.0}$ $TCID_{50}$:18 ml, 20 ml, 25 ml, or 28 ml) for the virus strains and the volume of culture solution; specific to Canine Parvovirus vaccine strain, inoculating in the dosage ratio of $10^{5.0}$$TCID_{50}$: 50-150 ml (such as, $10^{5.0}$$TCID_{50}$: 60 ml, 70 ml, 80 ml, 90 ml, 100 ml, 110 ml, 120 ml, 130 ml, or 140 ml) for the virus strains and the volume of culture solution; and specific to Canine Infectious Hepatitis virus vaccine strain, inoculating in the dosage ratio of $10^{5.0}$$TCID_{50}$: 50-150 ml (such as, $10^{5.0}$$TCID_{50}$: 60 ml, 70 ml, 80 ml, 90 ml, 100 ml, 110 ml, 120 ml, 130 ml, or 140 ml) for the virus strains and the volume of culture solution.

In some embodiments, in step (i), specific to the Canine Distemper virus vaccine strain, the culture solution is the DMEM containing 1.5-2.5 v/v % (such as, 1.8 v/v %, 2.0 v/v %, 2.2 v/v %, and 2.4 v/v %) new-born calf serum; specific to the Canine Parvovirus vaccine strain, the culture solution is the RPMI Medium 1640 containing 2-8 v/v % (such as, 3 v/v %, 4 v/v %, 5 v/v %, 6 v/v %, and 7 v/v %) new-born calf serum; specific to the Canine Infectious Hepatitis virus vaccine strain, the culture solution is the DMEM containing 1.5-2.5 v/v % (such as, 1.8 v/v %, 2.0 v/v %, 2.2 v/v %, and 2.4 v/v %) new-born calf serum.

In some embodiments, in step (i), specific to the Canine Distemper virus vaccine strain or the Canine Infectious Hepatitis virus vaccine strain, the temperature of culture is 32-34° C. (such as, 32.5° C., 33° C. and 33.5° C.); specific to Canine Parvovirus vaccine strain, the temperature of culture is 36.5-37.5° C. (such as, 36.7° C., 36.9° C., 37.1° C., and 37.3° C.).

In some embodiments, in step (i), the pH value of culture is 7.0-7.5 (such as, 7.1, 7.2, 7.3, and 7.4).

In some embodiments, in step (i), the DO value of culture is 40-50% (such as, 42%, 44%, 46%, and 48%).

In some embodiments, in step (i), when the culture is roller bottle culture, the culture is conducted under the condition of 9-12 Revolutions/Hour (such as, 10 Revolutions/Hour and 11 Revolutions/Hour).

In some embodiments, in step (i), when the culture is suspension culture, the culture is conducted under the condition of 25-35 Revolutions/Minute (such as, 26 Revolutions/Minute, 28 Revolutions/Minute, 30 Revolutions/Minute, 32 Revolutions/Minute and 34 Revolutions/Minute).

In some embodiments, in step (i), specific to the Canine Distemper virus vaccine strain, the Vero cell is from monolayer Vero cell; specific to the Canine Parvovirus vaccine strain, the F81 cell is from monolayer F81 cell; specific to the Canine Infectious Hepatitis virus vaccine strain, the MDCK cell is from monolayer MDCK cell.

In some embodiments, in step (i), specific to the Canine Distemper virus vaccine strains, using trypsin to digest the monolayer Vero cells and then inoculating the vaccine strains; specific to the Canine Parvovirus vaccine strains, using trypsin to digest the monolayer F81 cells and then inoculating the vaccine strains; and specific to the Canine Infectious Hepatitis virus vaccine strains, using trypsin to digest the monolayer MDCK cells and then inoculating the vaccine strains.

In some embodiments, in step (i), performing sterility test on the crude viral liquid of the vaccine strains.

In some embodiments, in step (i), the preparation step of the culture cells is: amplificating culture the seed cells of the cultured culture cells, to obtain the culture cells of amplification culture.

In some embodiments, the amplification culture is conducted under 36.5-37.5° C. (such as, 36.7° C., 36.9° C., 37.1° C. and 37.3° C.).

In some embodiments, the amplification culture is conducted under 9-12 Revolutions/Hour (such as, 10 Revolutions/Hour and 11 Revolutions/Hour) in roller bottle.

In some embodiments, specific to the Canine Distemper virus vaccine strain, the culture solution of the amplification culture is the DMEM containing 6-10 v/v % (such as, 7 v/v %, 8 v/v % and 9 v/v %) new-born calf serum; specific to the Canine Parvovirus vaccine strain, the culture solution of the amplification culture is the RPMI Medium 1640 containing 6-10 v/v % (such as, 7 v/v %, 8 v/v %, and 9 v/v %) new-born calf serum; specific to the Canine Infectious Hepatitis virus vaccine strain, the culture solution of the amplification culture is the DMEM containing 6-10 v/v % (such as, 7 v/v %, 8 v/v %, and 9 v/v %) new-born calf serum.

In some embodiments, the time of the amplification culture is 18-30 h (such as, 20 h, 22 h, 24 h, 26 h, and 28 h).

In some embodiments, when the culture is suspension culture, the culture cell of the amplification culture is digested by trypsin and then transferred into bioreactor for continuing culture.

In some embodiments, in the bioreactor, the temperature of the continuing culture is 36-38° C. (such as, 36.5° C., 37° C., and 37.5° C.).

In some embodiments, in the bioreactor, the pH value of the continuing culture is 7.0-7.5 (such as, 7.1, 7.2, 7.3, and 7.4).

In some embodiments, in the bioreactor, the DO value of the continuing culture is 40-50% (such as, 42%, 44%, 46%, and 48%).

In some embodiments, in the bioreactor, the continuing culture is conducted under the condition of 25-35 Revolutions/Minute (such as, 26 Revolutions/Minute, 28 Revolutions/Minute, 30 Revolutions/Minute, 32 Revolutions/Minute, and 34 Revolutions/Minute).

In some embodiments, in step (ii), the crude viral liquid of the vaccine strains is frozen and thawed for 1-3 times and then purified.

In some embodiments, in step (ii), the method of purification is: using the filter membrane with a diameter of 0.22-0.45 μm to filter and remove cells and cell debris, to obtain the purified viral liquid of vaccine strains.

In some embodiments, specific to the Canine Distemper virus vaccine strain, the virus content in the purified viral liquid of vaccine strains is $\geq 10^{5.0} TCID_{50}$/ml; specific to the Canine Parvovirus vaccine strain, the virus content in the purified viral liquid of vaccine strains is $\geq 10^{6.0} TCID_{50}$/ml; specific to the Canine Infectious Hepatitis virus vaccine strain, the virus content in the purified viral liquid of vaccine strains is $\geq 10^{6.0} TCID_{50}$/ml.

In some embodiments, mixing the combination of vaccine strains and the excipients to obtain the vaccine composition.

In some embodiments, the preparation method of the freeze-drying protectant comprises the following steps:

preparing the first aqueous solution comprising 4-6 mg/mL (such as, 4.5 mg/mL, 5.0 mg/mL, and 5.5 mg/mL) polyvinyl pyrrolidone and 16-24 mg/mL (such as, 18.0 mg/mL, 20.0 mg/mL, and 22.0 mg/mL) sorbitol;

preparing the second aqueous solution comprising 6-14 mg/mL (such as, 8.0 mg/mL, 10.0 mg/mL, and 12.0 mg/mL) glycine, 60-100 mg/mL (such as, 65.0 mg/mL, 70.0 mg/mL, 75.0 mg/mL, 80.0 mg/mL, 85.0 mg/mL, 90.0 mg/mL, and 95.0 mg/mL) sucrose and 60-120 mg/mL (such as, 65.0 mg/mL, 70.0 mg/mL, 75.0 mg/mL, 80.0 mg/mL, 85.0 mg/mL, 90.0 mg/mL, 95.0 mg/mL, 100.0 mg/mL, 105.0 mg/mL, 110.0 mg/mL, and 115.0 mg/mL) trehalose; and mixing the first aqueous solution and the second aqueous solution in the volume ratio of 1:0.8-1.2 (such as, 1:0.9, 1.0, or 1.1) to obtain the freeze-drying protectant.

In some embodiments, after being sterilized, the first aqueous solution is used.

In some embodiments, after being sterilized at 110-120° C. (such as, 112° C., 114° C., 116° C., and 118° C.), the first aqueous solution is used.

In some embodiments, after being sterilizing, the second aqueous solution is used.

In some embodiments, after being filtered and sterilized, the second aqueous solution is used.

In some embodiments, the vaccine compositions are dried to obtain the dried vaccine compositions.

In some embodiments, drying is freeze vacuum drying.

In some embodiments, the freeze vacuum drying comprises the following steps:

(a) performing freezing on the vaccine compositions to obtain the frozen vaccine compositions;

(b) performing sublimation drying with temperature elevated by stages on the frozen vaccine compositions under a vacuum condition to obtain the preliminarily dried vaccine compositions;

(c) performing sublimation drying on the preliminarily dried vaccine compositions at a normal temperature under a vacuum condition to obtain the dried vaccine compositions.

In some embodiments, in step (a), performing freezing on the vaccine compositions at −50° C. to −40° C. (such as, −48° C., −46° C., −44° C., and −42° C.).

In some embodiments, in step (a), the duration time of freezing is 1.5-2.5 h (such as, 1.6 h, 1.8 h, 2.0 h, 2.2 h, and 2.4 h).

In some embodiments, in step (b), the vacuum condition is 8 pa-10 pa (such as, 8.5 pa, 9.0 pa, and 9.5 pa).

In some embodiments, in step (b), performing the first sublimation at −30° C. to −26° C. (such as, −29° C., −28° C., and −27° C.), performing the second sublimation at −17° C. to −13° C. (such as, −16° C., −15° C., and −14° C.), and the third sublimation at 6-10° C. (such as, 7° C., 8° C., and 9° C.) on the frozen vaccine compositions.

In some embodiments, in step (b), the time of the first sublimation is 4-8 h (such as, 5 h, 6 h, and 7 h).

In some embodiments, in step (b), the time required for the temperature to rise from a range of −50° C. to −40° C., to the other arrange of −30° C. to −26° C. is 0.5-1.5 h (such as, 0.6 h, 0.8 h, 1.0 h, 1.2 h, and 1.4 h).

In some embodiments, in step (b), the time of the second sublimation is 4-8 h (such as, 5 h, 6 h, and 7 h).

In some embodiments, in step (b), the time required for the temperature to rise from a range of −30° C. to −26° C. to the other arrange of −17° C. to −13° C. is 0.5-1.5 h (such as, 0.6 h, 0.8 h, 1.0 h, 1.2 h, and 1.4 h).

In some embodiments, in step (b), the time of the third sublimation is 2-6 h (such as, 3.0 h, 3.5 h, 4.0 h, 4.5 h, 5.0 h, and 5.5 h).

In some embodiments, in step (b), the time required for the temperature to rise from a range of −17° C. to −13° C. to the other range of 6-10° C. is 0.5-1.5 h (such as, 0.6 h, 0.8 h, 1.0 h, 1.2 h, and 1.4 h).

In some embodiments, in step (c), the vacuum condition is 8 pa-10 pa (such as, 8.5 pa, 9.0 pa, and 9.5 pa).

In some embodiments, in step (c), the temperature of sublimation is 25-30° C. (such as, 26° C., 27° C., 28° C., and 29° C.).

In some embodiments, in step (c), the time of sublimation is 1-3 h (such as, 1.5 h, 2.0 h, and 2.5 h).

In some embodiments, the time required for the temperature to rise from 6-10° C. in step (b) to 25-30° C. in step (c) is 0.5-1.5 h (such as, 0.6 h, 0.8 h, 1.0 h, 1.2 h, and 1.4 h).

In the fourth aspect, the present invention provides use of the vaccine strains of the first aspect of the present invention, the vaccine compositions of the second aspect of the present invention, or the preparation method of the third aspect of the present invention in preparing the preparations for preventing Canine Distemper, Canine Parvovirus Enteritis and Canine Infectious Hepatitis, or for preventing Canine Distemper and Canine Parvovirus Enteritis, or for preventing Canine Parvovirus Enteritis and Canine Infectious Hepatitis.

In some embodiments, the Canine Distemper is Canidae animal Canine Distemper, Mustelidae animal Canine Distemper, or Felidae animal Canine Distemper.

In some embodiments, the Canine Distemper is mink Canine Distemper, dog Canine Distemper, or fox Canine Distemper.

In some embodiments, the Canine Parvovirus Enteritis is Canidae animal Canine Parvovirus Enteritis, Mustelidae animal Canine Parvovirus Enteritis, or Felidae animal Canine Parvovirus Enteritis.

In some embodiments, the Canine Parvovirus Enteritis is mink Canine Parvovirus Enteritis, dog Canine Parvovirus Enteritis or fox Canine Parvovirus Enteritis.

In some embodiments, the Canine Infectious Hepatitis is Canidae animal Canine Infectious Hepatitis, Mustelidae animal Canine Infectious Hepatitis or Felidae animal Canine Infectious Hepatitis.

In some embodiments, the Canine Infectious Hepatitis is mink Canine Infectious Hepatitis, dog Canine Infectious Hepatitis or fox Canine Infectious Hepatitis.

DETAILED DESCRIPTION OF THE EMBODIMENTS

In order to make the purpose, technical solutions and advantages of the present invention more clear, the embodiments of the present invention will be further described in detail in combination with Figures bellow.

The current "Chinese Veterinary Pharmacopoeia" referred to in the present invention is "Veterinary Pharmacopoeia of the People's Republic of China", 2015 Edition, Section three, Published by China Agriculture Press. The $TCID_{50}$ of the present invention is obtained by calculating according to Reed-Muench method. Canine Distemper high virulent CDV-v strain is a strain internally isolated by Liaoning Yikang Biological Corporation Limited, and the $ID_{50}$ data is obtained by detecting clinically healthy beagle dogs. Canine Parvovirus high virulent CPV-v strains a strain internally isolated by Liaoning Yikang Biological Corporation Limited, and the $TCID_{50}$ data is obtained by determining F81 cells. Canine Viral Hepatitis virus CAV-1v strain a strain internally isolated by Liaoning Yikang Biological Corporation Limited, and the $TCID_{50}$ data is obtained by determining MDCK cells. DMEM is purchased from GIBCO with the batch number 1928536; RPMI Medium 1640 is purchased from GIBCO with the batch number 1900496; newborn calf serum is purchased from Bovogen Biologicals Pty Ltd with the batch number 1507D; trypsin is purchased from GIBCO with the batch number 1902509. Vero cell and F81 cell are purchased from China Institute of Veterinary Drug Control, and preserved by Liaoning Yikang Biological Corporation Limited. MDCK cell is purchased from Changchun Military Veterinary Research Institute, passaged and preserved by Liaoning Yikang Biological Corporation Limited.

Figure 7:
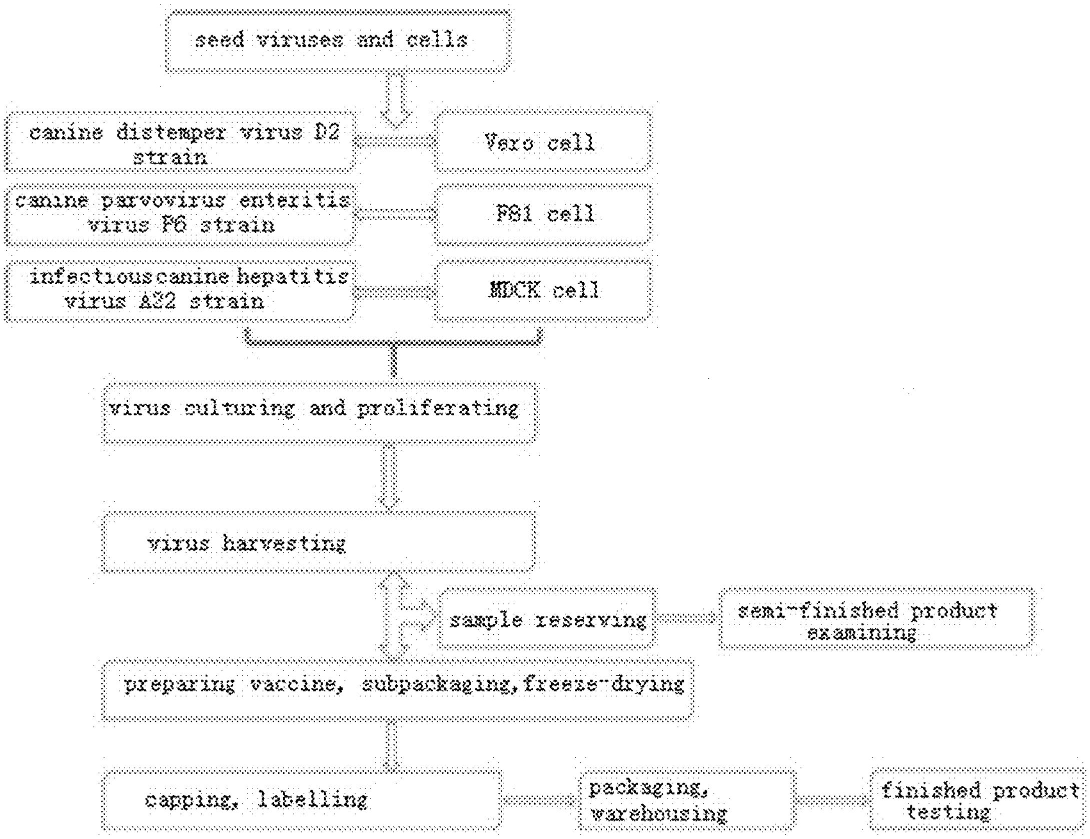
FIG. 7 is the production process roadmap of the triple live vaccine of the present invention.

See FIG. 7 for the production process roadmap of the triple live vaccine of the present invention.

Example 1. The Acquisition of the Original Strains of Canine Distemper Virus (1) Case: the young dogs at a dog farm of a dog professional cooperative in Liaoyang city, Liaoning province, get sick with the symptoms of high fever, depression, snot and eye secretions, and neurological symptom appearing in the later stage. Judging from the symptoms, they are suspected of suffering from Canine Distemper.

(2) Virus isolation: taking the brain tissues of sick dogs, using sterilized normal saline to rinse the brain tissues for 3 times; adding the brain tissues into sterilized cold normal saline at a ratio of Ig tissue: 10 ml, and putting them into tissue mixer to fully crush the brain tissues at 10000-12000 r/min; after freezing and thawing them repeatedly bellow −15° C. for three times, using three layers of sterilized gauzes to filter them for two times, collecting the filtrate, centrifuging at 12000 r/min at 4° C. for 30 min; collecting the supernatant, adding the filtered and sterilized penicillin with a final concentration of 1000 IU/ml and streptomycin with a final concentration of 1000 μg/ml, subpackaging, and obtaining tissue fluid a.

Figure 1:
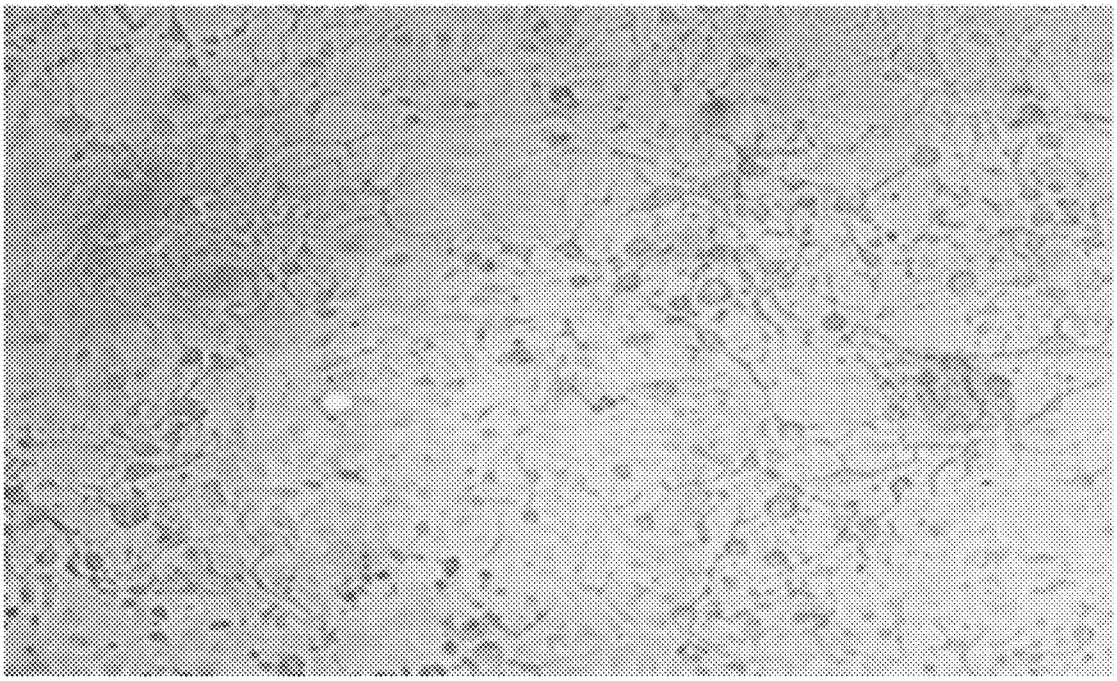
FIG. 1 is the photograph of the isolated and cultured Canine Distemper virus to be identified.

Inoculating the above-mentioned tissue fluid a on Vero cells for isolation and culturing, wherein the culture solution is the DMEM containing 2 v/v % new-born calf serum, and the inoculum size is 1 v/v %. Placing them in an incubator containing 5% $CO_2$ at 37° C., and observing. No visible cytopathy is observed in the blind passaging of four generations. When the blind passaging of the $5^{th}$ generation, arachnoid cytopathy appears in the cells (see FIG. 1). On such basis, further amplifying one generation, totally culturing and collecting 200 ml of cell culture solution a, as virus seed for use. Most of them are added with sucrose skimmed milk protectant and then freeze-dried for preservation. The virus contained in cell culture solution a is called as strain a.

Using the serum free DMEM cell culture solution to dilute the above-mentioned cell culture solution a with 10-fold serial dilution. Taking the $10^{-1}$-$10^{-8}$ dilutability of the cell culture solution to respectively inoculate the 96 holes Vero cell culture plates that have grown into a good monolayer and from which the cell culture solution has been discarded. Inoculating 8 holes for each dilutability with 0.1 ml per hole, and meanwhile setting 8 holes as normal cell control. After placing it in the incubator containing 5% $CO_2$ at 33° C. to adsorb for 1 hour, supplementing 0.1 ml DMEM cell culture solution containing 4% new-born calf serum in each hole, and placing it in the incubator containing 5% $CO_2$ at 33° C. to culture and observe for 6 days, and observing CPE conditions each day. Calculating the $TCID_{50}$ by Reed-Muench method. As a result, the virus content is $10^{5.5}TCID_{50}/0.1$ ml.

Figure 2:
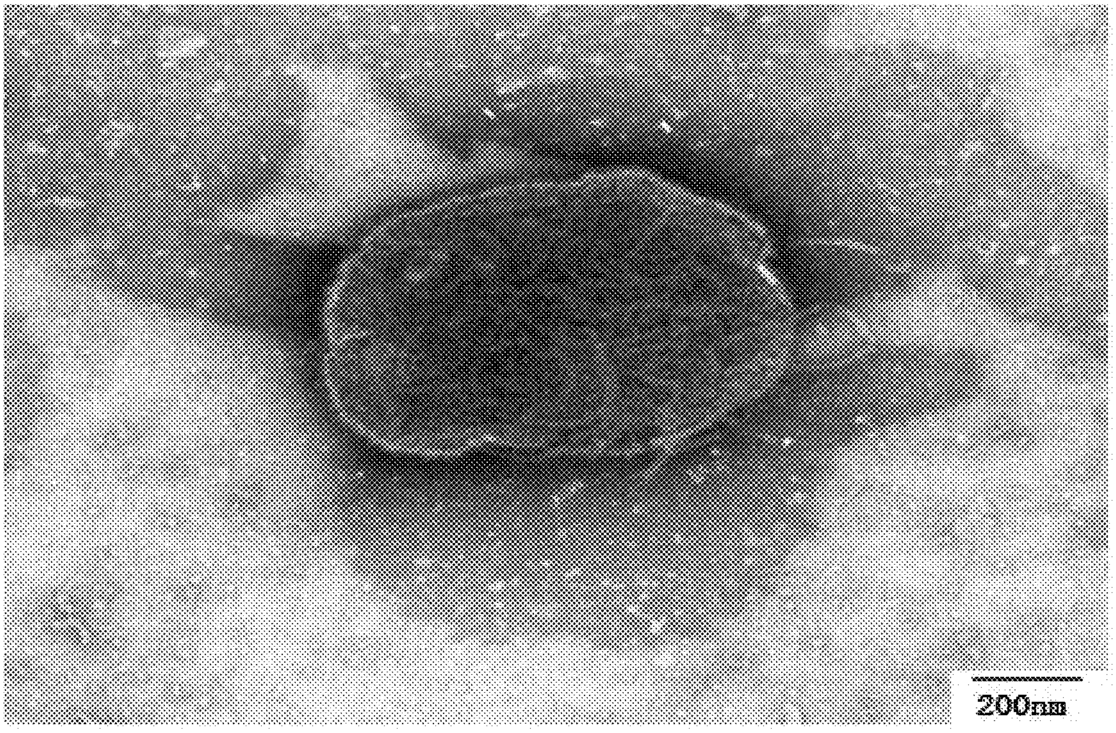
FIG. 2 is the electron microscopic photograph of the isolated strain of Canine Distemper virus to be identified.

(3) Morphologic observation: using phosphotungstic acid to stain the strains a in the supernatant of the cell culture solution a of step (2) and further making negative staining, and using transmission electron microscope to observe. Judging from the morphological observation, the morphology is diverse, mostly elliptical, with capsules and circular spikes thereon. The photograph of one of them is shown in FIG. 2, and the strain a is Canine Distemper virus.

(4) Molecular biological identification: specific to the H gene segment of the hemagglutinin protein of Canine Distemper virus, designing the primers Fla and Ria with the following sequences to perform RT-PCR detection on the strains a in the supernatant of cell culture solution a. Then agarose gel electrophoresis is performed, and the size of electrophoresis band is 335 bp, which conforms to the length of the H gene of Canine Distemper. By the further judgment, the strain a is Canine Distemper virus.

```
                                        (SEQ ID NO.1)
Fla: 5'-GATAAAGCATGTCATTATAGTCCTAA-3'

                                        (SEQ ID NO.2)
Rla: 5'-CTTGAGCTTTCGACCCTTC-3'
```

(5) Specificity test: incubating 0.1 ml of Canine Distemper virus antiserum (neutralization titer is not less than 1:128), Canine. Parvovirus antiserum (neutralization titer is not less than 1:64), Canine Viral Hepatitis virus antiserum (all neutralization titers are not less than 1:128), rabies virus antiserum (neutralization titer is not less than 40 IU/ml) and healthy dog negative serum (the negative serum is the serum of a four-month-old healthy dog without immunizing any vaccine) (the above-mentioned serum are gifted by the Virus Room of Military Veterinary Research Institute) respectively with 0.1 ml cell culture solution a, and using 0.1 ml of the same virus solution without adding any serum for the virus control holes. Subsequently, inoculating them in the Vero cells that have grown into a good monolayer, wherein the culture solution is the DMEM containing 2 v/v % new-born calf serum, placing them in the incubator containing 5% $CO_2$ at 37° C. to observe for 5 days. Except for that the cells inoculated with the virus solution incubated with Canine Distemper virus antiserum and the normal cells without inoculating do not develop cytopathy, all cells of other groups develop cytopathy. It illustrates that the isolated and obtained virus is Canine Distemper virus. It can be seen that the strain a is Canine Distemper virus.

(6) Regression test: using sterilized normal saline to dilute the cell culture solution a (containing strain a) of step (2) to a virus content of $10^{4.0}$ $TCID_{50}$/ml, and inoculating four healthy young dogs of 2-3 months old with CDV antibody negative (SN<1:2) with a inoculum size of 2.0 ml. The inoculation method is an intraperitoneal injection. Observing time after inoculation is 28 days. And the symptoms are as follows: three inoculated dogs have excessive eye secretions and nose secretions; four dogs have fever to 38.9° C.-39.6° C., no deaths occurred, the course of disease lasted 5 days and then they recovered. The second fever does not occur. None of the four control dogs that were fed in the same way and not injected with the virus get sick. These symptoms are typical Canine Distemper symptoms, from which it can be judged that the strain a is Canine Distemper virus.

(7) Confirmed diagnosis: the strain a is Canine Distemper virus based on the comprehensive judgment of the previous test and identification.

Example 2. Domestication of Canine Distemper Virus Strain and Tests on the Biochemical and Hereditary Alterations of the Strain (1) Virus subculturing: successively subculturing the cell culture solution a (containing strain a) of Example 1 on Vero cell to 150 generations. The specific steps are as follows: discarding growth solution (the composition is DMEM containing 2 v/v % new-born calf serum) from the Vero cells that have grown into a monolayer; inoculating the cell culture solution a of Example 1 in 5 v/v % inoculum size, placing it in the incubator containing 5% $CO_2$ at 33° C. to adsorb for one hour, and then adding the DMEM cell maintenance solution containing 2 v/v % new-born calf serum, and culturing in the incubator containing 5% $CO_2$ at 33° C. for 5-6 days; harvesting the progeny virus when more than 90% the cells appear CPE, successively passaging 150 generations. The 150$^{th}$ generation is named as D2 strain.

(2) Tests on virus viability: Using the serum free DMEM cell culture solution to dilute the 120$^{th}$, 135$^{th}$ and 150$^{th}$ generation virus seed respectively with 10-fold serial dilution, using the same method as the step (2) of Example 1 to calculate and obtain the followings: the virus contents of the attenuated virus of the 120$^{th}$, 135$^{th}$ and 150$^{th}$ generation are $10^{6.30}$ $TCID_{50}$/ml, $10^{6.12}$ $TCID_{50}$/ml, and $10^{6.00}$ $TCID_{50}$/ml, respectively.

The gradual decrease of the virus content measured according to the infectivity also shows that the virulence of the virus is gradually weakening.

(3) Tests on virus safety: using sterilized normal saline to dilute the cell culture solution of the virus of the 100$^{th}$, 120$^{th}$, 135$^{th}$ and 150$^{th}$ generation to $10^{5.0}$ $TCID_{50}$/ml respectively, subcutaneously inoculating five healthy and susceptible dogs over 2 months old with 4.0 ml each dog by injecting on a plurality of spots, meanwhile, setting four control dogs without inoculating. Isolating and observing them for 21 days, and respectively recording the clinical manifestation of the dogs each group. The result is as follows: the incidence of the virus group of the 100$^{th}$ generation is 2/5, symptoms represent as fever, depression and increased nose and eye secretions. The incidence of the virus group of the 120$^{th}$ generation is 1/5, symptoms represent as fever and depression. The incidence of the virus group of the 135$^{th}$ generation, the virus group of the 150$^{th}$ generation and control is zero, respectively, without the disease symptoms. This illustrates that the virus has lost virulence after 135 generations, therefore, the virulence of 150 generations will be weaker, and it may be safe to use as a live vaccine.

(4) Tests on immunogenicity and immune protection: using sterilized normal saline to respectively dilute the cell culture solution of the virus of the 135$^{th}$ and 150$^{th}$ generation to $10^{4.0}$ $TCID_{50}$/ml, subcutaneously injecting to inoculate five clinically healthy dogs of 6 weeks old with Canine Distemper virus antibody negative respectively, and meanwhile setting five dogs without inoculating virus as a control group. On the 21st day after immunization, collecting blood and isolating serum, and using neutralization test to perform the titer determination (estimation of potency) of serum neutralizing antibody. The steps are as follows: taking the cell culture solution a (containing strain a) in the step (2) of Example 1 with a content of $10^{4.0}$ $TCID_{50}$/ml as the antigen (containing 200$TCID_{50}$), performing two-fold dilution to serum for using. The immune effect is judged by inoculating the Vero cells to observe CPE, and the antibody titer was calculated according to Reed-Muench method. After collecting blood, each dog of the immune group and the control group is inoculated with 5.0 ml (content is 2 $ID_{50}$/ml) with CDV-v strain respectively through intraperitoneal injection, isolated for been fed and observed for 28 days, and the clinical manifestations are recorded.

After immunization for 21 days, the neutralizing antibody titer of the dogs for the 135$^{th}$ generation virus group is 1:76.1, 1:64, 1:76.1, 1:76.1 and 1:90.5 respectively, and all dogs are healthy and live. After immunization for 21 days, the neutralizing antibody titer of the dogs for the 150$^{th}$ generation virus group is 1:64, 1:76.1, 1:97.2, 1:76.1 and 1:64 respectively, and all dogs are healthy and live. In the virus challenge control group, no neutralizing antibody is detected in the first dog, and the symptoms are as follows: fever, depression, increased nose and eye secretions and death; no neutralizing antibody is detected in the second dog, and the symptoms are as follows: fever, depression and death; no neutralizing antibody is detected in the third dog, the symptoms are as follows: fever, depression, increased nose and eye secretions and death; after immunization for 21 days, the neutralizing antibody titer of the fourth dog is 1:2, the symptoms are: fever, depression and death; after immunization for 21 days, the neutralizing antibody titer of the fifth dog is 1:2, the symptoms are: fever, depression and death. As can be seen, after passaging 135 generations, the virulence of the Canine Distemper virus isolated in the present invention disappears, and the immunogenicity is good.

(5) Sterility test: randomly selecting five bottles of the attenuated frozen virus seeds of the Canine Distemper virus of the 150$^{th}$ generation (D2 strain), and performing test according to the appendix of the current "Chinese Veterinary Pharmacopoeia". The result is that the five virus seeds cultured in TG medium, GA medium and GP medium all grow aseptically.

(6) *Mycoplasma* test: using *mycoplasma* medium. Randomly selecting the attenuated frozen virus seeds of the Canine Distemper virus of the 150$^{th}$ generation (D2 strain), and performing test according to the appendix of the current "Chinese Veterinary Pharmacopoeia".

The result is as follows: no "fried egg"-like *mycoplasma* colony is shown on the agar solid plate. Positive control (*mycoplasma* hyorhinis) is that "fried egg"-like *mycoplasma* colonies are shown on the solid medium; the liquid medium turns yellow, and is acidic with pH 6.35. Negative control is that no "fried egg"-like *mycoplasma* colony is shown on solid medium; the pH of the liquid medium is 7.48.

(7) Exogenous virus test: using the 150$^{th}$ generation virus seeds (D2 strain) as a template to make PCR amplification specific to Canine Parvovirus VP2 gene and Canine Viral Hepatitis virus spike protein gene, and make RT-PCR amplification specific to Canine Parainfluenza virus N gene, Rabies virus N gene, and Canine Distemper virus H gene. The result is as follows: only the amplification result specific to Canine Distemper virus H gene is positive.

(8) Specificity identification of attenuated virus: using serum free DMEM to dilute the 150$^{th}$ generation attenuated virus to 200 $TCID_{50}$/0.1 ml, and determining the virus specificity with the same method as in step (5) of Example 1. The result is as follows: except for the cell inoculated with the virus solution incubated with the antiserum of Canine Distemper virus and the normal cells without inoculating do not develop cytopathy, all cells of other groups develop cytopathy. It illustrates that the virus of D2 strain is Canine Distemper virus.

(9) Gene sequence analysis of attenuated virus: using the upstream and downstream primer F2a and R2a of the full length (1735 bp) sequence of Canine Distemper virus H gene to conduct nucleic acid amplification to the viruses of attenuated 120$^{th}$ generation and 150$^{th}$ generation, sequencing, and comparing the sequences. The result is as follows: the homology between the two is 99.3%.

```
                                        (SEQ ID NO.3)
F2a: 5'-ATGCTCTCCTACCAAGATAAGGTG-3'

                                        (SEQ ID NO.4)
R2a: 5'-TCAAGGTTTTGAACGGTTACATGAG-3'
```

Using the passaged and attenuated virus seeds of the $150^{th}$ generation as the candidate strain to prepare Canine Distemper live vaccine.

(10) Microorganism deposition: submitting the isolated and domesticated Canine Distemper virus D2 strains to the depositary institution designated by patent procedure in the present invention. It is Canine Distemper virus D2 strain with the microorganism depositary number CGMCC No. 19397; it is classified and named as Canine Distemper virus; the depositary time is Mar. 30, 2020; the depositary unit is China General Microbiological Culture Collection Center; the depositary address is Institute of Microbiology, Chinese Academy of Sciences, No. 3, Courtyard 1, Beichen West Road, Chaoyang District, Beijing, China. The strain is called as Canine Distemper virus D2 strain, CDV D2 strain or D2 strain.

Example 3. Roller Bottle Culture of Canine Distemper Virus Strain (D2 Strain)

(a) Cell amplification culture: amplifying the cultured Vero seed cells in a roller bottle for culturing at the temperature of 37° C. for 24 hours, wherein the culture solution is the DMEM containing 8 v/v % new-born calf serum and the rotation rate is controlled to be 10-11 Revolutions/Hour. (b) Inoculating: taking the roller bottle with the well grown Vero cell monolayer, discarding the culture solution, inoculating the produced seed virus (i.e., Canine Distemper virus D2 strain prepared in Example 2) in 5 v/v % inoculum size (content is $10^{4.0}$ $TCID_{50}$/ml), placing it at 33° C. to adsorb for one hour, adding the DMEM cell maintenance solution containing 2 v/v % new-born calf serum, spinning-culturing at 33° C. at a rotation rate of 10-11 Revolutions/Hour. (c) Harvesting: observing cytopathy daily; when CPE reaches more than 90%, harvesting the virus culture solution, freezing and thawing twice at −20° C. Meanwhile, the samples are taken for sterility test and virus content determination. After ensuring sterility, performing subsequent steps. (d) Sterility test: performing test according to the appendix of the current “Chinese Veterinary Pharmacopoeia”. The result is no bacterial growth. (e) Virus content: using the same method as step (2) of Example 1 to determine the virus content, and ensuring that virus content is $10^{5.0}$ $TCID_{50}$/ml. (f) Purifying: filtering the virus culture solution obtained in the step (c) through a filter membrane with a diameter of 0.22 μm to obtain D2 strain Canine Distemper virus solution with cells and debris removed.

Example 4. Suspension Culture of Canine Distemper Virus Strain (D2 Strain)

(a) The preparation of cells: amplifying the resuscitated-cultured Vero cells in a roller bottle for culturing at the temperature of 37° C., wherein the culture solution is the DMEM containing 8 v/v % new-born calf serum and the rotation rate is controlled to be 10-11 Revolutions/Hour. Upon the cells grow to be a dense monolayer, they are digested with 240 USP U/mg trypsin and dispersed. When the cell viability is not less than 95%, the Vero cells are transferred in the bioreactor at a inoculating density (seeding density) of $2.0\text{-}10.0\times10^5$ cells/ml, and the dosage of carrier is 2-5 g/L, and the cell culture parameters of the reactor (the temperature is 37±0.5° C., pH value is 7.2±0.1, DO value is 45±5% and the rotation rate is 30 r/min) are set. Samples were taken every 24 h for cell observation and counting. (b) Inoculating virus and harvesting: when the Vero cells grow to be a dense monolayer in the bioreactor and the cell density reaches $3.0\times10^6$ cells/ml, the precipitate is discharged out of the culture solution. The D2 strains of Canine Distemper virus prepared in Example 2 are inoculated according to MOI=0.005-0.01, supplemented with the DMEM cell maintenance solution containing 2 v/v % new-born calf serum for virus culture, and the parameters of the reactor for virus culture (the temperature is 33±0.5° C., pH value is 7.2±0.1, DO value is 45±5% and the rotation rate is 30 r/min) are set. Harvesting them when culturing for 96-120 h or the cytopathy reaches more than 90%, freezing and thawing twice at −20° C. Meanwhile the samples are taken for sterility test and virus content determination. Before preparing vaccine, the carrier and cell debris are removed from the virus antigen solution qualified by inspection through aseptic centrifugation or filtration. (c) Sterility test: performing test according to the appendix of the current “Chinese Veterinary Pharmacopoeia”, the result is no bacterial growth. (d) Virus content: the same method as in step (2) of Example 1 is used to determine the virus content to ensure that virus content is $\geq10^{5.0}$ $TCID_{50}$/ml. (e) Purifying: filtering the virus culture solution obtained in step (b) through a filter membrane with a diameter of 0.22 μm to obtain D2 strain Canine Distemper virus solution with cells and debris removed.

Example 5. Acquisition of the Original Strains of Canine Parvovirus (1) Case: one young dog case appearing the suspected clinical symptoms of Canine Parvovirus is collected in a dog farm in Liaoning province, and it gets sick. The symptoms are: fever, depression and mild diarrhea. Judging according to the symptoms, it is suspected to suffer from the Canine Parvovirus Enteritis.

(2) Virus isolation: taking the intestinal tissues of the sick animal, using sterilized normal saline to rinse the intestinal tissues for three times; adding the intestinal tissues in sterilized cold normal saline at a ratio of Ig tissues: 10 ml; putting them into a tissue bender to fully crush the intestinal tissues at 10000-12000 r/min; after freezing and thawing them repeatedly bellow −15° C. for three times, using three layers of sterilized gauzes to filter them twice, collecting the filtrate, centrifuging at 12000 r/min at 4° C. for 30 min; collecting the supernatant, adding the 1000 IU/ml penicillin and 1000 μg/ml streptomycin in a final concentration, subpackaging, and obtaining the tissue fluid b.

Figure 3:
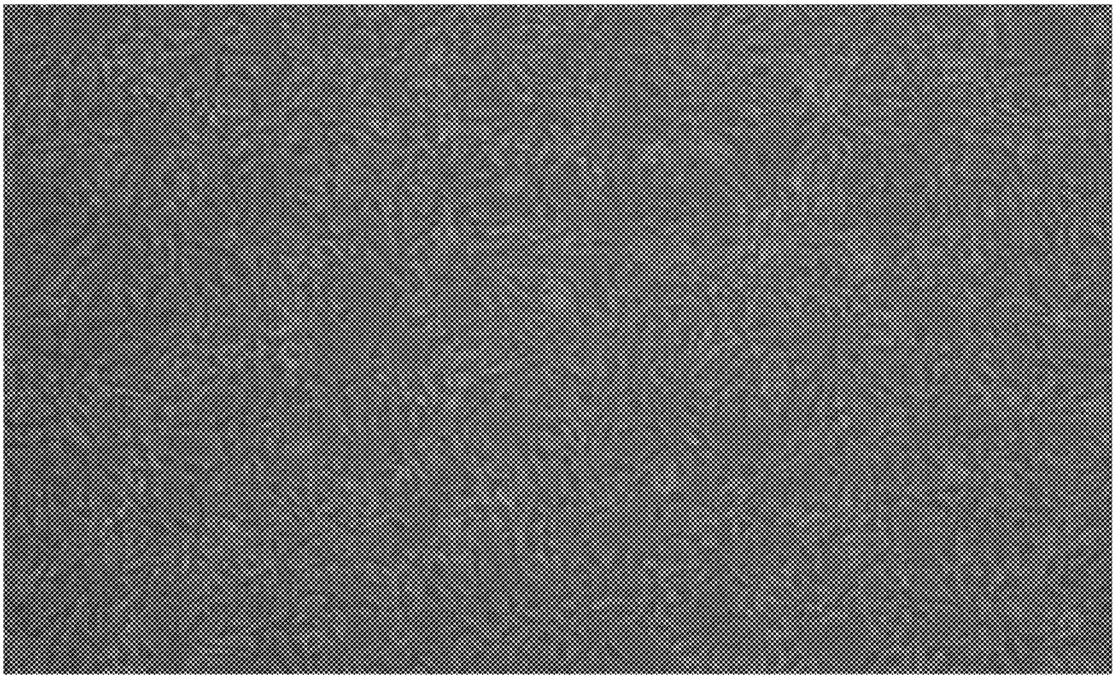
FIG. 3 is the photograph of the isolated and cultured Canine Parvovirus to be identified.

Using F81 cells for separating. F81 cells are digested and cultured according to the conventional method, and the culture solution is 8% RPMI Medium 1640. When passaging and dispersing cells, they are synchronously inoculated on the above tissue fluid b, and the inoculum size is 1 v/v %, meanwhile setting the healthy cells without inoculating virus as a control. Placing them in the incubator containing 5% $CO_2$ at 37° C. to culture and observe for 3-5 days, harvesting the cultures for identification. The visible cytopathy appears in the $1^{st}$ generation, and arachnoid cytopathy appears in the cells (see FIG. 3). On this basis, further amplifying one generation, 200 ml cell culture solution b is cultured and collected in total, most of which are added with sucrose skimmed milk protectant and then freeze-dried for preservation. The virus contained in the cell culture solution b is called as strain b.

Using the RPMI Medium 1640 cell culture solution containing 8% new-born calf serum to dilute the above-mentioned cell culture solution b with 10-fold serial dilution. Taking the $10^{-1}$-$10^{-8}$ dilutability of the cell culture solution to respectively inoculate the 96 holes F81 cell culture plates, inoculating 8 holes for each dilutability with 0.1 ml per hole, and meanwhile setting 8 holes as normal cell control. Placing them in the incubator containing 5% $CO_2$ at 37° C. to culture and observe for 5 days, and observing the CPE conditions each day. Calculating the $TCID_{50}$ according to Reed-Muench method. As a result, the virus content is $10^{5.2}TCID_{50}/0.1$ ml.

Figure 4:
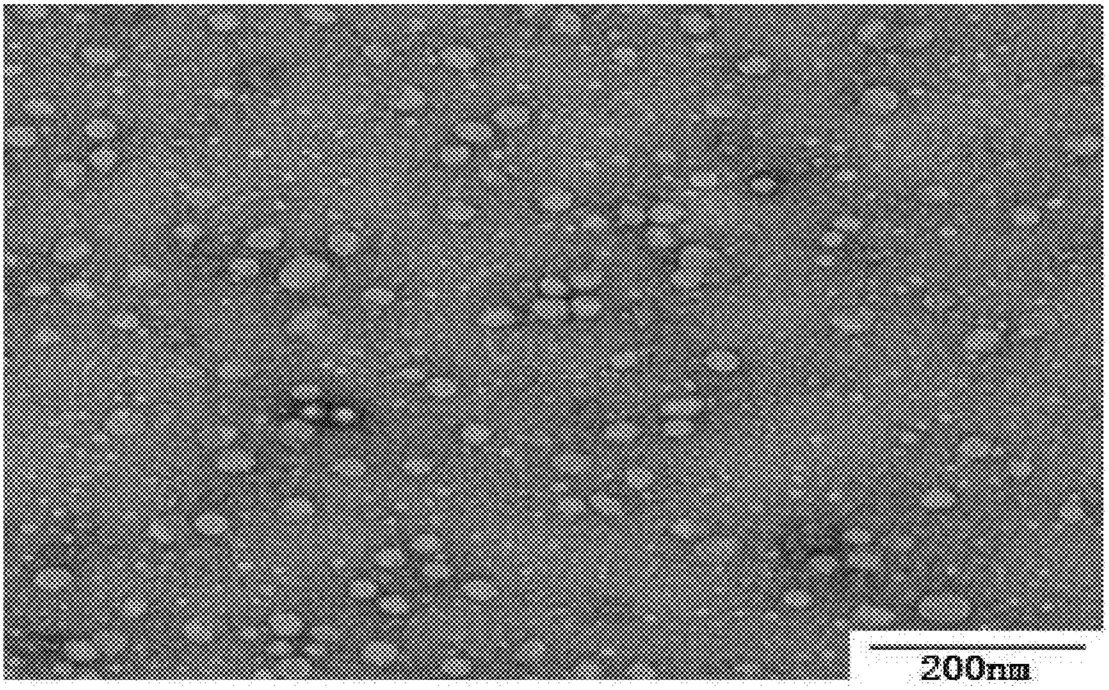
FIG. 4 is the electron microscopic photograph of the isolated strain of Canine Parvovirus to be identified.

(3) Morphologic observation: using phosphotungstic acid to stain the strain b in the supernatant of the cell culture solution b of step (2) and further making negative staining, and using a transmission electron microscope to observe it. The photograph is referred to FIG. 4. As observed and judged from the morphologically, the strain b is Canine Parvovirus.

(4) Molecular biological identification: specific to the VP2 gene of Canine Parvovirus, designing the primers P1b and P2b with the following sequences to perform RT-PCR detection on the strain b in the supernatant of cell culture solution b. Then performing agarose gel electrophoresis, and the size of electrophoresis band is 390 bp, which conforms to the length of the VP2 gene of Canine Parvovirus. Making further judgment, strain b is Canine Parvovirus. Sequencing the amplified products, and the maximal homology between the obtained sequence and the nucleic acid sequence of Canine Parvovirus strain published on NCBI is up to 99.3%. It is thus convinced that strain b is Canine Parvovirus.

```
                                   (SEQ ID NO.5)
P1b: 5'-CTCAGCCACCAACTAAAG-3'

                                   (SEQ ID NO.6)
P2b: 5'-GTAAGCCCAATGCTCTAT-3'
```

(5) Specificity test: incubating 0.1 ml Canine Parvovirus positive serum (the neutralization titer is not less than 1:128), Canine Distemper virus positive serum (the neutralization titer is not less than 1:128), Canine Viral Hepatitis virus positive serum (the neutralization titer is not less than 1:128), rabies virus positive serum (the neutralization titer is not less than 40 IU/ml) and healthy dog negative serum (the negative serum is a serum of four-month-old healthy dog without immunizing with any vaccine) (the above-mentioned sera are gifted from the virus Room of Military Veterinary Research Institute), respectively, with 0.1 ml cell culture solution b at 37° C. for one hour, synchronously inoculating them on F81 cells. The culture solution is 8% RPMI Medium 1640. Meanwhile, setting the normal cell control (the F81 cells without inoculating with any virus) and the virus control (inoculating the cell culture solution b into F81 cells without adding serum) 6 holes each, placing them in the incubator containing 5% $CO_2$ at 37° C. to culture and observe for 5 days. As a result, except for the cell culture solution b incubated with Canine Parvovirus positive serum and the normal cell control do not make F81 cell generate cytopathy, all other cells in tests show netting, crushing and shedding, illustrating that the isolated virus is Canine Parvovirus. It can be seen that strain b is Canine Parvovirus.

(6) Regression test: using sterilized normal saline to dilute the cell culture solution b (containing strain b) of step (2) to a virus content of $10^{5.0}$ $TCID_{50}$/ml, inoculating four healthy young dogs of 2-4 months old with Canine Parvovirus antibody negative (SN<1:2) with an inoculum size of 2.0 ml. The inoculation method is orally administration. Observing time is 14 days after inoculation, and the symptoms of the animal are as follows: at the $5^{th}$ or $6^{th}$ day of feeding and observing, three inoculated dogs develop mild enteritis one after another, accompanied by fever symptom, and the course of the disease lasted for 5 days and then they recover. None of four control dogs without injecting virus with the same feeding method gets sick. These symptoms are typical Canine Parvovirus Enteritis, it can thus be judged that the strain b is Canine Parvovirus virus.

(7) Confirmed diagnosis: the strain b is Canine Parvovirus based on the comprehensive judgment of the previous test and identification.

Example 6. Domestication of Canine Parvovirus Strain and Tests on the Biochemical and Hereditary Alterations of the Strains (1) Virus subculturing: successively subculturing the cell culture solution b (containing strain b) of step (2) of Example 5 on F81 cells to 220 generations, the specific steps are as follows: the culture solution is 8% RPMI Medium 1640, inoculating the cell culture solution b on the F81 cell monolayer with 1 v/v % dosage. The culture condition is as follows: placing them in the incubator containing 5% $CO_2$ at 37° C. They are cultured and observed in the incubator for 2-3 days. When CPE reaches more than 90%, the progeny virus is harvested, and successively passaged for 220 generations. The $220^{th}$ generation is named as P6 strain. The virus seeds of is the attenuated passage $220^{th}$ generations are used as the candidate strains for preparing Canine Parvovirus live vaccine.

(2) Tests on virus viability: using the same method as in step (2) of Example 5 to determine the $TCID_{50}$ of the cell culture solutions of the $180^{th}$, $200^{th}$ and $220^{th}$ generation virus seeds. Results are that the virus contents determined in the $180^{th}$, $200^{th}$ and $220^{th}$ virus culture solutions are $10^{6.71}$ $TCID_{50}$/ml, $10^{6.33}$ $TCID_{50}$/ml and $10^{6.41}$ $TCID_{50}$/ml, respectively. The virus content measured according to infection capability is decreased gradually, which further illustrates that the virulence of virus is weaken gradually.

(3) Tests on virus safety: taking the cell culture solutions of the $150^{th}$, $180^{th}$, $200^{th}$ and $220^{th}$ generation virus, respectively, using the same method as in step (2) of Example 5, calculating $TCID_{50}$ and using sterilized normal saline to dilute them to $10^{6.0}$ $TCID_{50}$/ml, respectively. Orally inoculating five healthy susceptible dogs of 2-4 month age with CPV neutralizing antibody titer not more than 1:2 with 4.0 ml for each dog and fasting without water-depriving for 24 hours, meanwhile, setting four control dogs without inoculating. Isolating and observing them for 14 days, and respectively recording the clinical manifestation of the dogs of each group. The results are as follows: 3/5 of the dogs inoculated with the cell culture solutions of $150^{th}$ generation virus get sick, and the symptoms are mild diarrhea. 5/5 of the dogs inoculated with the cell culture solutions of both $180^{th}$ and $220^{th}$ generation viruses are healthy and alive, and no significant difference is found between them and control dogs. The cell culture solutions of both $180^{th}$ and $220^{th}$ generation viruses have no virulence to young dogs. These indicate that this virus has no pathogenicity and side effects. The virus has lost virulence after passaging 180 generations, therefore, the virulence will be weaker after the virus passages for 220 generations, and it may be safe to use as a live vaccine.

(4) Tests on immunogenicity and immune protection: respectively using sterilized normal saline to dilute the cell culture solution of the virus seeds of the $180^{th}$ and $220^{th}$ generations to $10^{5.0}$ $TCID_{50}$/ml, subcutaneously inoculating five healthy and susceptible dogs of 6 weeks old with CPV antibody negative, each with 1.0 ml, respectively, meanwhile setting five dogs without injecting virus as controls. On the 21st day after immunization, collecting the blood and isolating the serum, and conducting the titer determination of serum neutralizing antibody by the neutralization tests, the steps are as follows: taking the cell culture solution b (containing strain b) in step (2) of Example 5 as antigen (containing 200$TCID_{50}$), performing 2-fold dilution on the serum for use. The immune effect is judged by inoculating F81 cells to observe CPE, and the antibody titer was calculated according to Reed-Muench method.

After collecting blood, using CPV-v strain to respectively inoculate dogs of immune group and control group, each with 2.0 ml (the content is $10^{3.0}$$TCID_{50}$/ml) to through oral injection route, isolating, feeding and observing them for 14 days, and recording the clinical manifestation. As a result, both the $180^{th}$ and the $220^{th}$ generations of CPV can induce the organism to produce better neutralizing antibody, and the neutralizing antibody reaches 1:90.5 on the $21^{st}$ day, which has the effect of neutralizing the CPV in cells; all immuned dogs are healthy and alive after challenging high virulence, and all control dogs get sick and dead after challenging high virulence. Specifically, on the 21st day after immunization, the neutralizing antibody titers for the $180^{th}$ generation virus group are 1:45.3, 1:90.5, 1:76.1, 1:64 and 1:32 respectively, and all dogs are healthy and alive. On the 21st day after immunization, the neutralizing antibody titers for the $220^{th}$ generation virus group are 1:64, 1:76.1, 1:76.1, 1:53.8 and 1:78.8 respectively, and all dogs are healthy and alive. No neutralizing antibody is detected in the virus challenge control group; the symptoms of the first dog are depression, bowed back, loose stools in soy sauce color and death; the symptoms of the second dog are depression, vomiting, bowed back and acute death; the symptoms of the third dog are depression, loose stools in soy sauce color and death; the symptoms of the fourth dog are depression, vomiting, bowed back and death; the symptoms of the fifth dog are depression, loose stools in soy sauce color and death. As can be seen, the virulence of the Canine Parvovirus isolated in the present invention disappears, and the immunogenicity of it is good after passaging 180 generations.

(5) Sterility test: randomly selecting five bottles of the attenuated frozen cell culture solution of the Canine Parvovirus of the $220^{th}$ generation (P6 strain), and performing tests according to the appendix of the current “Chinese Veterinary Pharmacopoeia”. The result is that 5 virus seeds cultured in TG medium, GA medium and GP medium all grow aseptically.

(6) *Mycoplasma* test: using the *mycoplasma* medium. Randomly selecting the attenuated frozen cell culture solution of the Canine Parvovirus of the $220^{th}$ generation (P6 strain) and performing tests according to the appendix of the current “Chinese Veterinary Pharmacopoeia”. Results: no “fried egg”-like *mycoplasma* colony is shown in the agar solid plate culture. Positive control (*mycoplasma* hyorhinis) is that “fried egg”-like *mycoplasma* colonies are shown on solid medium; the liquid medium turns yellow, and is acidic with pH 6.35. Negative control is that no “fried egg”-like *mycoplasma* colony is shown on solid medium; the pH of the liquid medium is 7.48.

(7) Exogenous virus test: using the $220^{th}$ generation virus seeds (P6 strain) as a template to perform PCR amplification specific to Canine Parvovirus VP2 gene and Canine Viral Hepatitis virus spike protein gene, and perform RT-PCR amplification specific to Canine Parainfluenza virus N gene, Rabies virus N gene, and Canine Distemper virus H gene. Result: only the amplification result specific to Canine Parvovirus VP2 gene is positive.

(8) Specificity identification of attenuated virus: using 8% RPMI Medium 1640 to dilute the attenuated viruses (P6 strain) of $220^{th}$ generations to 200 $TCID_{50}$/0.1 ml, and using the same method as in step (5) of Example 5 to determine the virus specificity. Result: except for that the cell culture solution of the $220^{th}$ generation attenuated virus incubated with Canine Parvovirus positive serum and the normal cells control do not develop cytopathy to F81 cells, other cells in tests develop cytopathy. It illustrates that the virus of P6 strain is Canine Parvovirus.

(9) Gene sequence analysis of attenuated virus: using the upstream and downstream primer P1b and P2b of the full length sequence of Canine Parvovirus VP2 gene to conduct nucleic acid amplification to the virus of attenuated $180^{th}$ generation and $220^{th}$ generation, sequencing, and comparing the sequences. Result: the homology between the two is 99.7%. Using the passaged and attenuated virus seed of the $220^{th}$ generation as the candidate strains to prepare Canine Parvovirus live vaccine.

(10) Microorganism deposition: submitting the isolated and domesticated Canine Parvovirus P6 strain to the depositary institution designated by patent procedure in the present invention, it’s microorganism depositary number is CGMCC No. 19398; it is classified and named as Canine Parvovirus; the depositary time is Mar. 30, 2020; the depositary unit is China General Microbiological Culture Collection Center; the depositary address is Institute of Microbiology, Chinese Academy of Sciences, NO. 3, Courtyard 1, Beichen West Road, Chaoyang District, Beijing, China. The strain is called as Canine Parvovirus P6 strain, CPV P6 strain or P6 strain.

Example 7. Roller Bottle Culture of Canine Parvovirus Enteritis Strain (P6 Strain)

(a) Cell amplification culture: amplifying the cultured F81 seed cells in a roller bottle for culturing at the temperature of 37° C. for 24 hours, wherein the culture solution is the RPMI Medium 1640 containing 8 v/v % new-born calf serum and the rotation rate is controlled to be 10-11 Revolutions/Hour. (b) Inoculating: when the monolayer F81 overgrows in the cell roller bottle, discarding the culture solution, after using 240 USP U/mg trypsin to digest it, passaging in 1:2 ratio, adding the RPMI Medium 1640 containing 8 v/v % new-born calf serum, synchronously inoculating the produced virus seeds of parvovirus P6 strains of Example 6 (the content is $10^{5.0}$ $TCID_{50}$/ml) in F81 cell with 1 v/v % of inoculum size, spinning-culturing it at 37° C. with a rotation rate of 10-11 Revolutions/Hour. (c) Harvesting: observing cytopathy daily, harvesting the cell culture solution when CPE reaches more than 90%, freezing and thawing twice at −20° C. Meanwhile, the samples are taken for sterility test and virus content determination. After ensuring sterility, performing subsequent steps. (d) Sterility test: performing tests according to the appendix of the current “Chinese Veterinary Pharmacopoeia”. Result: no bacterial growth. (e) Virus content: using the same method as in step (2) of Example 5 to determine the virus content, and ensuring that the virus content is $\geq 10^{6.0}$ $TCID_{50}$/ml. (f) Purifying: filtering the virus culture solution obtained in step (c) through a filter membrane with a diameter of 0.22 μm to obtain P6 strain Canine Parvovirus virus solution with cells and debris removed.

Example 8. Suspension Culture of Canine Parvovirus Enteritis Strain Strain (P6 Strain)

(a) The preparation of cells: amplifying the resuscitated-cultured F81 cells in a roller bottle for culturing at the temperature of 37° C., wherein the culture solution is the RPMI Medium 1640 containing 8 v/v % new-born calf serum and the rotation rate is controlled to be 10-11 Revolutions/Hour. Upon the cells grow to be a dense monolayer, they are digested with 240 USP U/mg trypsin and dispersed. When the cell viability is not less than 95%, transferring F81 cell into a bioreactor with an inoculating density of 2.0-$10.0\times10^5$ cells/ml. The dosage of carrier is 2-5 g/L. Setting the parameters in the reactor for cell culturing (the temperature is 37±0.5° C., the pH value is 7.2±0.1, DO value is 45±5%, and the rotation rate is 30 r/min). Samples are taken every 24 h for cell observation and counting. (b) Inoculating virus and harvesting: when the F81 cells grow to be a dense monolayer in bioreactor and the cell density reaches $4.0\times10^6$ cells/ml, the precipitate is discharged out of the culture solution. Inoculating the Canine Parvovirus P6 strains prepared in Example 6 according to MOI=0.005-0.01, supplementing the RPMI Medium 1640 containing 2 v/v % new-born calf serum for virus culture, and setting the parameters in reactor for virus culture (the temperature is 37±0.5° C., pH value is 7.2±0.1, DO value is 45±5% and the rotation rate is 30 r/min). Harvesting them when culturing for 36-48 h or the cytopathy reaching more than 90%, freezing and thawing twice at −20° C. Meanwhile, the samples are taken for sterility test and virus content determination. Before preparing the vaccine, the carrier and cell debris are removed from the virus antigen solution qualified by inspection through aseptic centrifugation or filtration. (c) Sterility test: performing tests according to the appendix of the current "Chinese Veterinary Pharmacopoeia", the result: no bacterial growth. (d) Virus content: using the same method as in step (2) of Example 5 to determine the virus content to ensure that the virus content is $\geq10^{6.0}TCID_{50}$/ml. (e) Purifying: filtering the virus culture solution obtained in step (b) through a filter membrane with a diameter of 0.22 μm to obtain P6 strain Canine Parvovirus virus solution with cells and debris removed.

Example 9. Acquisition of the Original Strain of Canine Infectious Hepatitis (1) Case: one young dog case having the suspected Canine Infectious Hepatitis symptom is collected at a dog farm of the dog professional cooperative in Liaoyang city, Liaoning province with the symptom of mild diarrhea. Judging according to the symptom, it is suspected to suffer from Canine Infectious Hepatitis.

(2) Virus isolation: taking the intestinal tissues of the sick animal, using sterilized normal saline to rinse the intestinal tissues for three times; adding the intestinal tissues in the sterilized cold normal saline at a ratio of Ig tissues: 10 ml; putting them in a tissue bender to fully crush the intestinal tissues at 10000-12000 r/min; after freezing and thawing them repeatedly bellow −15° C. for three times, using the three layers of sterilized gauzes to filter them twice, collecting the filtrate, centrifuging them at 12000 r/min at 4° C. for 30 min; collecting the supernatant, adding the filtered and sterilized penicillin with 1000 IU/ml of the final concentration and streptomycin with 1000 μg/ml of the final concentration, subpackaging, and obtaining the tissue fluid c.

Figure 5:
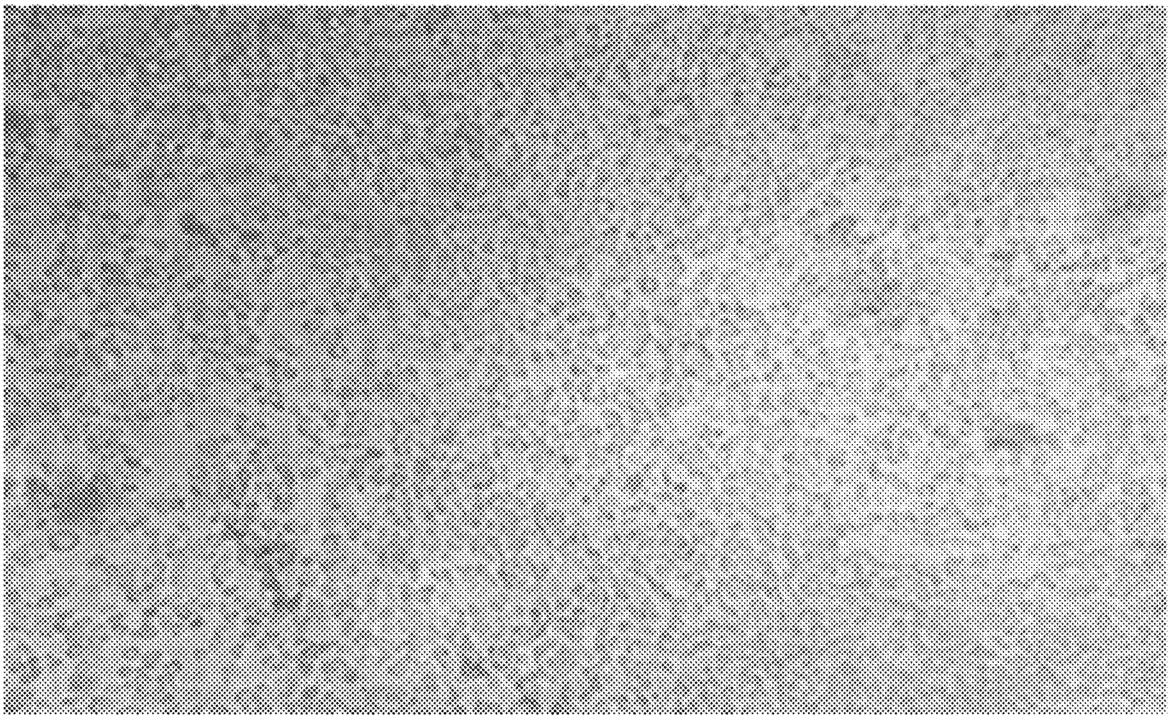
FIG. 5 is the photograph of the isolated and cultured suspected Canine Infectious Hepatitis virus.

Using MDCK cells for isolation. Taking MDCK cells for digesting and culturing according to the conventional method with the culture solution of DMEM. Inoculating the above tissue fluid c, the inoculum size is 1 v/v %, meanwhile setting the healthy cells without inoculating virus as a control. Placing them in the incubator containing 5% $CO_2$ at 37° C. to culture and observe for 2-3 days, harvesting the cultures, and performing identification. The 1st generation develops the visible cytopathy, the cytopathy that the cells have clustered like grape clusters with strong refractivity appears in the cells (see FIG. 5). On such basis, further amplifying one generation by inoculating at a ratio of 1 v/v %. 200 ml of the cell culture solution c is cultured and collected in total, most of which are added with sucrose skimmed milk protectant and then freeze-dried for preservation. The virus contained in cell culture solution c is called as strain c.

Using the serum free DMEM cell culture solution to dilute the above-mentioned cell culture solution c with 10-fold serial dilution. Taking the four dilutabilities of $10^{-4}$-$10^{-7}$ of the cell culture solution to respectively inoculate the 96 holes MDCK cell culture plates that have grown into a good monolayer and from which the cell culture solution has been discarded. Inoculating 8 holes for each dilutability with 0.1 ml per hole, meanwhile setting 8 holes as normal cell controls. Placing them in the incubator containing 5% $CO_2$ at 33° C. to adsorb for one hour, and supplementing 0.1 ml DMEM cell culture solution containing 4% new-born calf serum each hole, placing them in the incubator containing 5% $CO_2$ at 33° C. to culture and observe for 4 days. Calculating the $TCID_{50}$ according to the Reed-Muench method. Result: the virus content is $10^{5.5}TCID_{50}$/0.1 ml.

Figure 6:
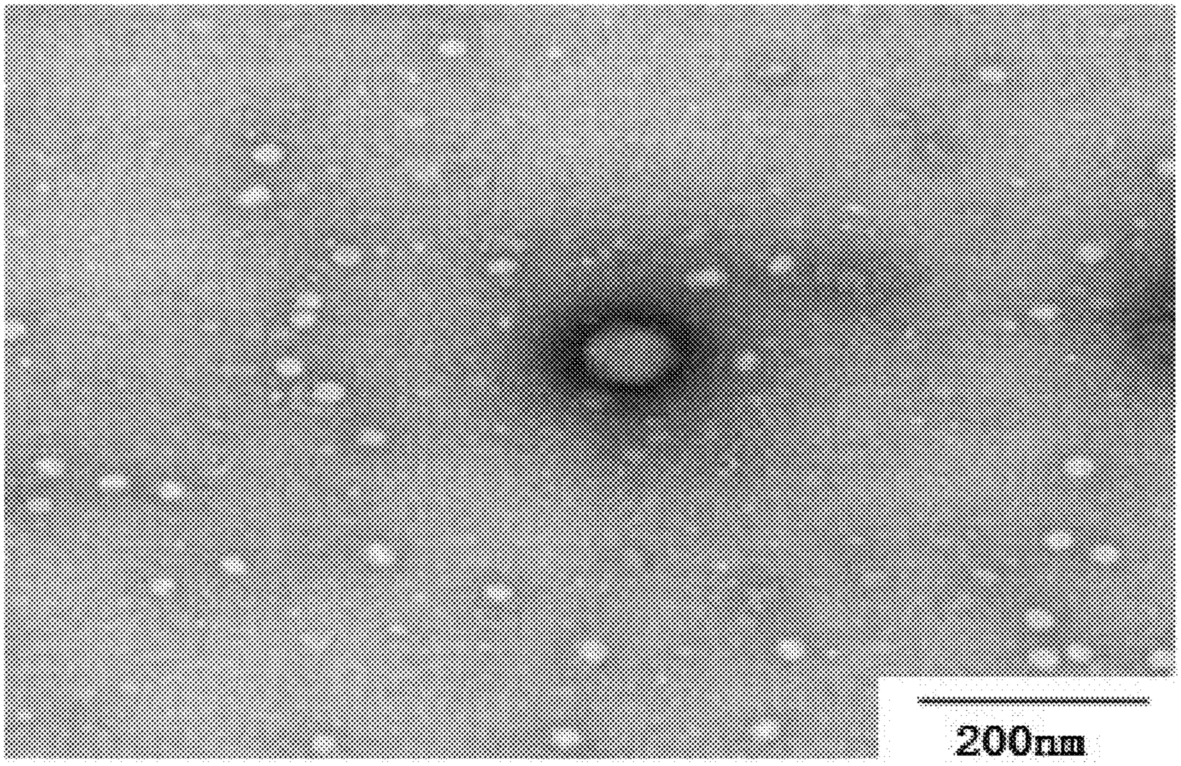
FIG. 6 is the electron microscopic photograph of the isolated strain of suspected Canine Infectious Hepatitis virus.

(3) Morphologic observation: using phosphotungstic acid to stain the cell culture solution c of step (2) and further making negative staining, and observing through transmission electron microscope. The photograph is referred to FIG. 6. As observed and judged from the morphologically, the strain c is Canine Infectious Hepatitis virus.

(4) Molecular biological identification: specific to the spike protein gene of Canine Infectious Hepatitis virus, designing the primers P1c and P1c with the following sequences to conduct RT-PCR detection to the strain c, and then conduct agarose gel electrophoresis. The size of electrophoresis band is 1019 bp, which conforms to the length of the spike protein gene of Canine Infectious Hepatitis virus. By the further judgment, strain c is Canine Infectious Hepatitis virus.

```
                                        (SEQ ID NO.7)
P1c: 5'-CGCGCTGAACATTACTACCTTGTC-3'

                                        (SEQ ID NO.8)
P2c: 5'-CTTCGTGTCCGCTTCATG-3'
```

(5) Specificity test: respectively incubating 0.1 ml Canine Parvovirus positive serum (the neutralization titer is not less than 1:64), Canine Distemper virus positive serum (the neutralization titer is not less than 1:128), Canine Viral Hepatitis virus positive serum (the neutralization titer is not less than 1:128), rabies virus positive serum (the neutralization titer is not less than 40 IU/ml) or healthy dog negative serum (the negative serum is the serum of four-month-old healthy dog without immuning any vaccine) (the above-mentioned sera are gifted from the virus Room of Military Veterinary Research Institute) with 0.1 ml cell culture solution c at 37° C. for 1 hour, inoculating them in the DMEM cells that have grown into a good monolayer, the culture solution is DMEM. Meanwhile, setting the normal cell control (the MDCK cells without inoculating any virus) and the virus control (inoculating the cell culture solution c in MDCK cells without adding serum) 6 holes each, placing them in the incubator containing 5% $CO_2$ at 37° C. to observe for 4 days. Results: except for that the cell culture solution c incubated with Canine Infectious Hepatitis positive serum and the normal cell control do not make MDCK cells develop cytopathy, other cells in tests develop cytopathy that the cells have clustered like grape clusters with strong refractivity, illustrating that the isolated virus is Canine Infectious Hepatitis virus. It can be seen that strain c is Canine Infectious Hepatitis virus.

(6) Regression test: using sterilized normal saline to dilute the cell culture solution c (containing strain c) of step (2) to have a virus content of $10^{5.0}$ $TCID_{50}$/ml, inoculating four healthy young dogs of 2-3 months old with Canine Infectious Hepatitis antibody negative (SN<1:2) with a inoculum size of 4.0 ml. The inoculation method is oral administration and intranasal administration, each of 2.0 ml. Observing time is 14 days after inoculation. At the $5^{th}$, $9^{th}$, $14^{th}$ day of feeding and observing, three inoculated dogs develop mild diarrhea one after another, accompanied by mild fever, and the course of the disease lasted for 2 days and then they recover. None of one inoculated dog and four control dogs without injecting virus with the same feeding method gets sick. These symptoms are typical Canine Infectious Hepatitis, it can thus be judged that the strain c is Canine Infectious Hepatitis virus.

(7) Confirmed diagnosis: the strain c is Canine Infectious Hepatitis virus based on the comprehensive judgment of the previous test and identification.

Example 10. The Domestication of Canine Infectious Hepatitis Virus Strains and Tests on the Biochemical and Hereditary Alterations of the Strains (1) Virus subculturing: successively subculturing the cell culture solution c (containing strain c) of step (2) of Example 9 on MDCK cells to 130 generations, the specific steps are as follows: the culture solution is the DMEM containing 8% new-born calf serum, inoculating the cell culture solution c of the step (2) of Example 9 on the MDCK cell monolayer with a dosage of 1 v/v %. The culture condition is: placing it in the incubator containing 5% $CO_2$ at 37° C. to culture and observing for 2-3 days. When the cytopathy reaches more than 90%, harvesting the progeny virus, successively passaging 130 generations. The $130^{th}$ generation is named as A22 strain. The passaged and attenuated virus seeds of the $130^{th}$ generations are used as the candidate strains for preparing Canine Infectious Hepatitis live vaccine.

(2) Tests on virus viability: determining the $TCID_{50}$ of the cell culture solution of the $100^{th}$, $115^{th}$ and $130^{th}$ generation virus seeds by the same method as in step (2) of Example 9. Result: the virus content determined in the $100^{th}$, $115^{th}$ and $130^{th}$ virus culture solution is $10^{6.3}$ $TCID_{50}$/ml, $10^{6.7}$ $TCID_{50}$/ml and $10^{6.4}$ $TCID_{50}$/ml, respectively.

(3) Tests on virus safety: taking the cell culture solution of the $80^{th}$, $100^{th}$, $115^{th}$ and $130^{th}$ generation virus, respectively, calculating $TCID_{50}$ by the same method as in step (2) of Example 9, and using sterilized normal saline to dilute them to $10^{6.0}$ $TCID_{50}$/ml, respectively. Inoculating five healthy susceptible dogs of 2-4 months old with Canine Infectious Hepatitis virus neutralizing antibody titer being not more than 1:2 through subcutaneous injection route, 1.0 ml for each dog. Meanwhile setting four control dogs without inoculating. Isolating and observing them for 14 days, and respectively recording clinical manifestation of the dogs of each group. Result: 4/5 of dogs of the $80^{th}$ generation virus group get sick with mild diarrhea; 1/5 of dogs of $100^{th}$ generation virus group get sick with mild diarrhea; the number of sick dogs of both $115^{th}$ and $130^{th}$ generation virus groups is zero, no abnormal performance.

(4) Tests on immunogenicity and immune protection: using sterilized normal saline to respectively dilute the cell culture solution of the virus seeds of the $115^{th}$ and $130^{th}$ generations to $10^{5.0}$ $TCID_{50}$/ml, subcutaneously injecting them to five clinically healthy dogs of 6 weeks old with Canine Infectious Hepatitis virus antibody negative respectively, injecting 1.0 ml for each dog, and meanwhile setting five dogs without injecting as a control group. On the 21st day after immunization, collecting blood and isolating serum, and conducting the titer determination of neutralizing antibody by neutralization tests, the steps are as follows: taking the cell virus solution c (containing strain c) in step (2) of Example 9 as an antigen (containing 200 $TCID_{50}$), performing two-fold dilution to serum for use. The immune effect is judged by inoculating MDCK cells to observe CPE, and the antibody titer is calculated according to the Reed-Muench method. After collecting blood, respectively inoculating each dog of immune group and control group with 2.0 ml of CAV-1v strains (the content is $10^{6.5}$ $TCID_{50}$/ml) 1.0 ml each for oral administration and intranasal administration. After challenging, isolating, feeding and observing them for 14 days, and recording clinical manifestation. Results: both the $115^{th}$ generations and the $130^{th}$ generations of Canine Infectious Hepatitis virus can induce the organism to produce better neutralizing antibody, which have the effect of neutralizing the Canine Infectious Hepatitis virus in cells; all immuned dogs are healthy and alive after challenging high virulence, and all control dogs get sick and dead after challenging high virulence. Specifically, on the 21st day after immunization, the neutralizing antibody titers for the $115^{th}$ generation virus group are 1:64, 1:76.1, 1:45.3, 1:64 and 1:90.5 respectively, and all dogs are healthy and alive. On the 21st day after immunization, the neutralizing antibody titers for the $130^{th}$ generation virus group are 1:53.8, 1:97.2, 1:32, 1:64 and 1:76.1 respectively, and all dogs are healthy and alive. In the virus challenge control group, no neutralizing antibody are detected, the appearances of all dogs are fever, diarrhea and death. As can be seen, after passaging 115 generations, the virulence of the Canine Viral Hepatitis virus isolated in the present invention disappears, and the immunogenicity is good.

(5) Sterility test: randomly selecting five bottles of the frozen cell culture solution of the attenuated virus seeds of the Canine Infectious Hepatitis virus of the $130^{th}$ generations (A22 strain), and performing tests according to the appendix of the current "Chinese Veterinary Pharmacopoeia". Result: five virus seeds cultured in TG medium, GA medium and GP medium all grow aseptically.

(6) *Mycoplasma* test: using the *mycoplasma* medium. Randomly selecting the frozen cell culture solution of the virus seeds of the attenuated Canine Infectious Hepatitis virus of the $130^{th}$ generation (A22 strain), and performing tests according to the appendix of the current "Chinese Veterinary Pharmacopoeia". Results: no "fried egg"-like *mycoplasma* colony is shown in the agar solid plate culture. Positive control (*mycoplasma hyorhinis*) is that "fried egg"-like *mycoplasma* colonies are shown on the solid medium;

the liquid medium turns yellow, and is acidic with pH 6.35. Negative control is that no "fried egg"-like *mycoplasma* colony is shown on the solid medium; the pH of the liquid medium is 7.48.

(7) Exogenous virus test: using the $130^{th}$ generation virus seeds (A22 strain) as a template to perform PCR amplification specific to Canine Parvovirus VP2 gene and Canine Viral Hepatitis virus spike protein gene, and perform RT-PCR amplification specific to Canine Parainfluenza virus N gene, Rabies virus N gene, and Canine Distemper virus H gene. Result: only the amplification result specific to Canine Viral Hepatitis virus spike protein gene is positive.

(8) Specificity identification of attenuated virus: using DMEM to dilute the $130^{th}$ generations attenuated virus (A22 strain) to 200 $TCID_{50}$/0.1 ml, and determining the virus specificity by the same method as in step (5) of Example 9. Result: except for that the cell culture solution incubated with Canine Parvoviru positive serum and the normal cells control do not develop cytopathy to MDCK cells, other cells in tests all develop cytopathy. It illustrates that A22 strain virus is Canine Infectious Hepatitis virus. The passaged and attenuated virus seeds of the $130^{th}$ generations are used as candidate strains for preparing Canine Distemper live vaccine.

(9) Microorganism deposition: submitting the isolated and domesticated Canine Infectious Hepatitisvirus A22 strain to the depositary institution designated by patent procedure in the present invention, it's microorganism depositary number is CGMCC No. 19396; it is classified and named as Canine Infectious Hepatitis virus; the depositary time is Mar. 30, 2020; the depositary unit is China General Microbiological Culture Collection Center; the depositary address is Institute of Microbiology, Chinese Academy of Sciences, No. 3, Courtyard 1, Beichen West Road, Chaoyang District, Beijing, China. The strain is called as Canine Infectious Hepatitis virus A22 strain, CAV A22 strain or A22 strain.

Example 11. Roller Bottle Culture of Canine Infectious Hepatitis Virus Strain (A22 Strain)

(a) Cell amplification culture: amplifying the cultured MDCK seed cells in a roller bottle for culturing at the temperature of 37° C. for 24 hours, wherein the culture solution is the DMEM containing 8 v/v % new-born calf serum, and the rotation rate is controlled to be 10-11 Revolutions/Hour. (b) Inoculating: taking the roller bottle with the well grown MDCK cell monolayer, discarding the culture solution, inoculating the producing seed virus (i.e., Canine Infectious Hepatitis virus A22 strain prepared in Example 10) with a inoculum size of 1 v/v % (the content is $10^{5.0}$ $TCID_{50}$/ml), placing them at 37° C. to adsorb for 1 hour, adding the DMEM containing 2 v/v % new-born calf serum, spinning-culturing them at 37° C., with a rotation rate of 10-11 Revolutions/Hour. (c) Harvesting: observing the cytopathy daily, harvesting the virus culture solution when CPE reaches more than 90%, freezing and thawing twice at −20° C. Meanwhile, the samples are taken for sterility test and virus content determination. After ensuring sterility, performing subsequent steps. (d) Sterility test: performing tests according to the appendix of the current "Chinese Veterinary Pharmacopoeia". Result: no bacterial growth. (e) Virus content: determining the virus content by the same method as in step (2) of Example 9 to ensure that the virus content is $\geq 10^{6.0}TCID_{50}$/ml. (f) Purifying: filtering the virus culture solution obtained in step (c) through a filter membrane with a diameter of 0.22 μm to obtain the A22 strain Canine Infectious Hepatitisvirus solution with cells and debris removed.

Example 12. Suspension Culture of Canine Infectious Hepatitis Virus Strain (A22 Strain)

(a) The preparation of cells: amplifying the resuscitated-cultured MDCK cells in a roller bottle for culturing at the temperature of 37° C., wherein the culture solution is the DMEM containing 8 v/v % new-born calf serum, and the rotation rate is controlled to be 10-11 Revolutions/Hour. Upon the cells grow to be a dense monolayer, they are digested with 240 USP U/mg trypsin and dispersed. When the cell viability is not less than 95%, transferring MDCK cells into a bioreactor with an inoculating density of 2.0-$10.0\times10^5$ cells/ml, the dosage of carrier is 2-5 g/L, and setting the parameters in the reactor for cell culturing (the temperature is 37±0.5° C., the pH value is 7.2±0.1, DO value is 45±5% and the rotation rate is 30 r/min). Samples are taken every 24 h for cell observation and counting. (b) Inoculating virus and harvesting: when the MDCK cells grow to be a dense monolayer in bioreactor and the cell density reaches $3.0\times10^6$ cells/ml, the precipitate is discharged out of the culture solution. Inoculating the Canine Infectious Hepatitis virus A22 strain prepared in Example 10 according to MOI=0.005-0.01, supplementing the DMEM cell maintenance solution containing 2 v/v % new-born calf serum for the virus culture, setting the parameters in the reactor for the virus culture (the temperature is 37±0.5° C., the pH value is 7.2±0.1, DO value is 45±5% and the rotation rate is 30 r/min). Harvesting them when culturing for 36-48 h or the cytopathy reaches more than 90%, freezing and thawing twice at −20° C. Meanwhile the samples are taken for sterility test and virus content determination. Before preparing vaccine, the carrier and cell debris are removed from the virus antigen solution qualified by inspection through aseptic centrifugation or filtration. (c) Sterility test: performing tests according to the appendix of the current "Chinese Veterinary Pharmacopoeia", Result: no bacterial growth. (d) Virus content: determining the virus content by the same method as in step (2) of Example 9 to ensure that the virus content is $\geq 10^{6.0}TCID_{50}$/ml. (e) Purifying: filtering the virus culture solution obtained in the step (b) through a filter membrane with a diameter of 0.22 μm to obtain the A22 strain Canine Infectious Hepatitis virus solution with cells and debris removed.

Example 13. Preparation of the Triple Live Vaccine of Canine Distemper Virus (D2 Strain), Canine Parvovirus (P6 Strain) and Canine Infectious Hepatitis Virus (A22 Strain)

(1) Preparation of Freeze-Drying Protectant

The preparation of freeze-drying protectant comprises: (a) the macromolecule part of the stabilizer: using 100 ml water for injection to solve and subpackage them, and then autoclaving them at 116° C. for 30 minutes. The ingredients comprise: 0.5 g polyvinyl pyrrolidone (PVP) and 2 g sorbitol. (b) the small molecule part of the stabilizer: using 100 ml water for injection to solve them, and then sterilizing them by filtration. The ingredients comprise: 1 g glycine, 8.3 g sucrose and 9.2 g trehalose. (c) when preparing the vaccine, mixing the solutions of the above two parts in a volume ratio of 1:1 to obtain the freeze-drying protectant.

(2) Preparation of Vaccine

Using sterilized normal saline to respectively dilute the Canine Distemper virus solutions qualified by inspection by the roller bottle culture in Example 3 or the suspension culture in Example 4 to the content of $10^{5.0}$ $TCID_{50}$/ml. Using sterilized normal saline to respectively dilute the Canine Parvovirus solutions qualified by inspection by the roller bottle culture in Example 7 or the suspension culture in Example 8 to the content of $10^{6.0}$ $TCID_{50}$/ml. Using sterilized normal saline to respectively dilute the Canine Infectious Hepatitis virus solution qualified by inspection by the roller bottle culture in Example 11 or the suspension culture in Example 12 to the content of $10^{6.0}$ $TCID_{50}$/ml. Mixing uniformly the diluted Canine Distemper virus solution, the diluted Canine Parvovirus solution, the diluted Canine Infectious Hepatitis virus solution and the sterilized freeze-drying protectant in a volume ratio of 5:1:1:3, and quantitatively subpackaging them. Each bottle comprises 2 ml of the mixed solution, and each bottle comprises one DOSE (the dosage for each dog). After subpackaging, quickly performing freeze vacuum drying, capping and sealing, and labeling.

The steps of freeze-drying are as follows: (i) prior to packing the products, reducing the temperature of the shelf of drying cabinet to about 0° C.; after packing the products, continuing to reduce the temperature of the shelf of drying cabinet to set the shelf temperature to be −45° C. This process needs to run for one hour, and keep it at this temperature for two hours to completely freeze the products, a total of three hours. (ii) One hour before the finish of product pre-freezing, starting to cool the cold trap. When the temperature of the cold trap reaches −40-−50° C., initiating the vacuum pump set (vacuum pump group) to conduct vacuumizing to reduce the pressure of freeze drying box to 8 pa-10 pa, ready for the first stage of sublimation drying of the product. (iii) At the beginning of the first stage of sublimation, the shelf temperature is −28° C., the sublimation interface does not exceed the disintegration temperature, and the pressure of the freeze drying box does not exceed 18 pa. The time of the first stage of sublimation drying is divided into three stages: raising the shelf temperature from −40° C. to −28° C., such process requires to run for one hour, and maintain at this temperature for 6 hours; raising the shelf temperature from −28° C. to −15° C., such process requires to run for 1 hour, and sublimation drying for 6 hours; raising the shelf temperature from −15° C. to 8° C., such process requires to run for 1 hour, and sublimation drying for 4 hours; the first stage of drying is finished, a total of 19 hours. (iv) desorption drying stage: in the second stage of sublimation drying, making the temperature of products reach about 28° C., such process requires to run for 1 hour, the maintaining time at such temperature is 2 hours to make the moisture content of the products reach 1-4%, and the freeze-drying procedure is finished.

In the present invention, the above-mentioned triple live vaccine is abbreviated as "triple vaccine".

Example 14. Finished Product Test on Triple Live Vaccine

Using the Canine Distemper virus solution of the roller bottle culture of Example 3, the Canine Parvovirus solution of the roller bottle culture of Example 7, the Canine Infectious Hepatitis virus solution of the roller bottle culture of Example 11, to independently prepare 3 batches of the triple live vaccines according to the method of Example 13, and performing the following tests.

(1) Character test: all 3 batches of triple vaccines present sponge-like loose masses, which are liable to be separated from bottle wall, and dissolve quickly after adding sterilized normal saline. (2) Sterility test: performing tests according to the appendix of the current "Chinese Veterinary Pharmacopoeia". Result: 3 batches of triple vaccines cultured in TG medium, GA medium and GP medium all grow aseptically.

(3) *Mycoplasma* test: performing tests according to the appendix of the current "Chinese Veterinary Pharmacopoeia". Results: no "fried egg"-like *mycoplasma* colony is shown in the agar solid plate culture of all 3 batches of triple vaccines. Positive control (*mycoplasma* hyorhinis) is that "fried egg"-like *mycoplasma* colonies are shown on solid medium; the liquid medium turns yellow, and is acidic with pH 6.35. Negative control is that no "fried egg"-ike *mycoplasma* colony is shown on solid medium; the pH of the liquid medium is 7.48. There is no *mycoplasma* grown for all 3 batches of triple vaccines.

(4) Exogenous virus test: performing tests according to the appendix of the current "Chinese Veterinary Pharmacopoeia", and taking respectively the nucleic acids of 3 batches of triple vaccines as templates to design primers respectively specific to Canine Parvovirus VP2 gene, Canine Viral Hepatitis virus spike protein gene, canine parainfluenza virus N gene, rabies virus N gene, and Canine Distemper virus H gene, and perform amplification in the RT-PCR mode. For the 3 batches of triple vaccines, only the amplification results specific to Canine Parvovirus VP2 gene, Canine Viral Hepatitis virus spike protein gene, and Canine Distemper virus H gene are positive, and the amplification results of other genes are negative.

Example 15. Determination of the Safety of Triple Live Vaccine

The reference standard for healthy dog inspection is that: the ears are cold, and the earholes are brown or dirty black; the eyes are clear and sparkle; Except for sleeping and just waking up, the nasal tip presents cold and wet; There is no odour like fishy smell in mouth, and the intraoral mucous membrane presents pink; the teeth are orderly, and the occluding is normal; the tail often wags; the anus is tightly closed and has no filth around; the hairs are clean and bright; the limbs are strong and powerful, walking naturally and stably, which conforms to the gait standard of its breed, without the phenomenon of staggering or falling down, and the inner sides of legs maintain clean; the physique is strong, the skeleton is strong, the muscles are full and strong, and the weight in the hands feels greater than it looks. Using the 3 batches of triple live vaccines of Example 14, respectively using sterilized normal saline to dilute the vaccine of one DOSE to the vaccine injection fluid 1 of 1.0 ml, and dilute the vaccine of five DOSEs to the vaccine injection fluid 2 of 1.0 ml. The following 6 groups of safety tests are performed. 5 beagle dogs or 10 Kunming mice are used as test animals and the healthy control group of the animals of the same species without inoculating. In each test, the test animals and the control animals are fed under the same conditions, see the following contents specifically.

(1) Safety test on the inoculation of a single dose: using vaccine injection fluid 1, respectively subcutaneously inoculating 2-month-old clinically healthy dogs with a single dose of the 3 batches of triple vaccines, the inoculum size is one DOSE/dog, and observing 14 days after inoculation. Results indicate that, all dogs subcutaneously injected with the 3 batches of triple vaccines of a single dose inoculation are healthy and alive, and they have no obvious differences from the dogs of the healthy control group in health condition with the good spirits, no abnormal behavior, normal stool, no abnormalities in food intake and drinking, normal body temperature, normal weight, good local injection absorption, no redness-swelling, no induration, no abnormal liver, spleen, kidney, heart, and gallbladder. The experiments prove that it is safe to subcutaneously inject all experimental dogs with the triple vaccines of a single dose inoculation.

(2) Safety test on single dose repeat inoculation: using the vaccine injection fluid 1, respectively subcutaneously inoculating two-month-old clinically healthy dogs with the 3 batches of triple vaccines of a single dose, the inoculum size is one DOSE/dog; after inoculating for 14 days, repeating to inoculate once with the inoculum size of one DOSE/dog; continuing to observe for 14 days. Results indicate that all dogs subcutaneously injected with the 3 batches of triple vaccines of a single dose repeated inoculation are healthy and alive, and they have no obvious difference from the dogs of healthy control group in health condition, with the good spirits, no abnormal behavior, normal stool, no abnormalities in food intake and drinking, normal body temperature, normal weight, good local injection absorption, no redness-swelling, no induration, no abnormal liver, spleen, kidney, heart, and gallbladder. The experiments prove that it is safe to subcutaneously inject all experimental dogs with the triple vaccines of a single dose repeated inoculation.

(3) Safety test on an overdose inoculation: using vaccine injection fluid 2, respectively subcutaneously inoculating 2-month-old clinically healthy dogs with the 3 batches of triple vaccines of overdose, the inoculum size is 10 DOSEs/dog, and observing for 14 days after inoculation. Results indicate that all dogs subcutaneously injected with the 3 batches of triple vaccines of overdose inoculation are healthy and alive, they have no obvious difference from the dogs of healthy control group in health condition, with the good spirits, no abnormal behavior, normal stool, no abnormalities in food intake and drinking, normal body temperature, normal weight, good local injection absorption, no redness-swelling, no induration, no abnormal liver, spleen, kidney; heart, and gallbladder. The experiments prove that it is safe to subcutaneously inject all experimental dogs with the triple vaccines of overdose inoculation.

(4) Safety test on pregnant dogs and lactating dogs: using vaccine injection fluid 2, respectively inoculating the pregnant dogs through the subcutaneous injection route with the 3 batches of triple vaccines of overdose and successively observing for 2 weeks, the inoculum size is 10 DOSEs/dog. Overdose-inoculating the lactating dogs with an inoculum size of 10 DOSEs/dog and successively observing for 2 weeks. Results indicate that all pregnant dogs and lactating dogs subcutaneously injected with the 3 batches of triple vaccines are healthy and alive, and they have no obvious difference from the dogs of healthy control group in health condition, with the good spirits, no abnormal behavior, normal stool, no abnormalities in food intake and drinking, normal body temperature, normal weight, good local injection absorption, no redness-swelling, no induration, no abnormal liver, spleen, kidney, heart, and gallbladder. There was no abortion or stillbirth in the pregnant dogs. The lactating dogs have not been weaned or lack of milk. The experiments prove that the triple vaccine immunization has no significant impact on the production performance of the pregnant dogs and lactating dogs.

(5) Safety test on the dogs not in a use-day age (baby dogs): using the vaccine injection fluid 2, respectively subcutaneously inoculating one-month-old healthy young dogs with the 3 batches of triple vaccines of overdose, the inoculum size is 10 DOSEs/dog, and observing for 14 days after inoculation. Results indicate that all young dogs injected with the 3 batches of triple vaccines of overdose through the subcutaneous route are healthy and alive, and they have no obvious difference from the dogs of healthy control group in health condition, with the good spirits, no abnormal behavior, normal stool, no abnormalities in food intake and drinking, normal body temperature, normal weight, good local injection absorption, no redness-swelling, no induration, no abnormal liver, spleen, kidney, heart, and gallbladder. The experiments prove that the triple vaccines are safe to one-month-old young dogs.

(6) Safety test on non-target animal mice: using the vaccine injection fluid 2, respectively subcutaneously inoculating the healthy mice with 3 batches of triple vaccines of overdose, the inoculum size is 2.0 ml (containing 10 DOSEs)/mouse, and observing for 14 days after inoculation. Results indicate that all mice subcutaneously injected with the 3 batches of triple vaccines of overdose inoculation are healthy and alive, they have no obvious difference from the mice of healthy control group in health condition, with the good spirits, no abnormal behavior, normal stool, no abnormalities in food intake and drinking, normal body temperature, normal weight, good local injection absorption, no redness-swelling, no induration, no abnormal liver, spleen, kidney, heart, and gallbladder. The experiments prove that the triple vaccines are safe to non-target animal mice. The results prove that all dogs and mice inoculated with the 3 batches of triple vaccines are healthy and alive, without redness-swelling at the injection local sites and the clinical abnormal reactions in the whole body. They have no obvious differences from the animals of healthy control group in health conditions such as food-intaking, drinking water, defecating and the like. Therefore, it is safe to use the triple live vaccines prepared in the present invention to inoculate dogs, and no adverse reactions are seen.

Example 16. Test on the Efficacy of Inoculating Route of the Triple Live Vaccine In the present Example, using sterilized normal saline to dilute the vaccine of one DOSE to 1.0 ml vaccine injection fluid for use, selecting 32 clinically healthy beagles of 2 month old, in which 30 beagles are divided into 6 groups randomly with 5 beagles each group. Wherein the 3 groups respectively use the 3 batches of triple vaccines of Example 14 for subcutaneously inject vaccine with one DOSE/beagle. For the other 3 groups, respectively use the 3 batches of triple vaccines of Example 14 for intramuscularly inject vaccine with one DOSE/beagle. The residual 2 beagles are used as blank controls, and are fed under the same conditions. On the 21st day after immunization, blood was collected from 32 beagles and the serum was separated. In accordance with the method of current "Chinese Veterinary Pharmacopoeia", (1) determining the neutralizing antibody titer of the serum of Canine Distemper virus, the step is as follows: taking the Canine Distemper virus D2 strains prepared in Example 2 as antigen (containing 200 $TCID_{50}$), respectively performing two-fold dilution on each serum for use, judging the immune effect through observing CPE by inoculating the Vero cells, and calculating the antibody titer according to Reed-Muench method. (2) determining the neutralizing antibody titer of the serum of Canine Parvovirus, the step is as follows: taking the Canine Parvovirus P6 strains prepared in Example 6 as antigen (containing 200

$TCID_{50}$), performing two-fold dilution on sera for use, judging the immune effect through observing CPE by inoculating F81 cells, and calculating the antibody titer according to Reed-Muench method. (3) determining the neutralizing antibody titer of the serum of Canine Viral Hepatitis, the step is as follows: taking the Canine Viral Hepatitis A22 strains prepared in Example 10 as antigen (containing 200 $TCID_{50}$), performing two-fold dilution on sera for use, judging the immune effect through observing CPE by inoculating MDCK cells, and calculating the antibody titer according to Reed-Muench method.

Results show that: using the intramuscular injection route to immune dogs, the average values of the neutralizing antibody titer of Canine Distemper virus D2 strains specific to three batches of the vaccines are 1:108.2, 1:104.0 and 1:107.6 respectively; the average values of the neutralizing antibody titer of Canine Parvovirus Enteritis virus P6 strains specific to three batches of the vaccines are 1:99.7, 1:90.5 and 1:97 respectively; and the average values of the neutralizing antibody titer of Canine Infectious Hepatitis virus A22 strains specific to three batches of the vaccines are 1:108.9, 1:104.0 and 1:111.4 respectively. Using the subcutaneous injection route to immune dogs, the average values of the neutralizing antibody titer of Canine Distemper virus D2 strains specific to three batches of the vaccines are 1:112.3, 1:111.4 and 1:115.4 respectively; the average values of the neutralizing antibody titer of Canine Parvovirus Enteritis virus P6 strains specific to three batches of the vaccines are 1:104.6, 1:100.4 and 1:104.0 respectively; and the average values of the neutralizing antibody titer of Canine Infectious Hepatitis virus A22 strain specific to three batches of the vaccines are 1:113.8, 1:107.6 and 1:119.4 respectively. For the control group, the neutralizing antibody to Canine Distemper virus D2 strains, the neutralizing antibody to Canine Parvovirus Enteritis virus P6 strains, the neutralizing antibody to Canine Infectious Hepatitis virus A22 strains are not detected. As can be seen, both inoculating routes can stimulate the effective immune protection to dogs, and the effect of subcutaneous injection is slightly better.

Example 17. Test on the Immune Efficacy and Protection of Triple Live Vaccine In the present Example, using sterilized normal saline to dilute the vaccine of one DOSE to 1.0 ml vaccine injection fluid for use, selecting 60 clinically healthy beagles of 2 months old to divide them into subgroups randomly with 5 beagles each subgroup. Dividing Canine Distemper virus challenge group, Canine Parvovirus virus challenge group or Canine Infectious Hepatitis virus challenge group into four subgroups respectively. In each group, respectively taking the vaccine of the first batch of the 3 batches of triple vaccines in Example 14 to subcutaneously inject the beagles of three subgroups with three doses of 0.01 DOSE/beagle, 0.1 DOSE/beagle and one DOSE/beagle, and setting 5 beagles without immunization as blank controls in another subgroup, and conducting feeding them under the same conditions. On the 21st day after immunization, blood was collected from 60 beagles, using the same method as that in Example 16 to respectively determine the serum neutralizing antibody titer to Canine Distemper virus, the serum neutralizing antibody titer to Canine Parvovirus and the serum neutralizing antibody titer to Canine Viral Hepatitis virus. After blood sampling, specific to Canine Distemper virus challenge group, intraperitoneally injecting all 20 beagles with 5.0 ml of the high virulent Canine Distemper CDV-v strains (the content is 2 $ID_{50}$/ml) respectively, and successively observing for 28 days. Specific to Canine Parvovirus challenge group, orally administering 2.0 ml of the high virulent Canine Parvovirus CPV-v strains (the content is $10^{3.0}$ $TCID_{50}$/ml) to all 20 beagles respectively, and successively observing for 14 days. Specific to Canine Infectious Hepatitis virus challenge group, orally and intranasally administering the high virulent Canine Viral Hepatitis virus CAV-1v strain 1.0 ml (the content is $10^{6.5}TCID_{50}$/ml) to all 20 beagles respectively, and successively observing for 14 days.

Results: (1) Canine Distemper virus challenge group: for the subgroup of 0.01 DOSE/beagle immunization, the serum neutralizing antibody titers are 1:53.8, 1:76.1, 1:53.8, 1:64 and 1:45.3 respectively, and the virus challenge protection is 80%; for the subgroup of 0.1 DOSE/beagle immunization, the serum neutralizing antibody titers are 1:64, 1:76.1, 1:90.5, 1:76.1 and 1:90.5 respectively, and the virus challenge protection is 100%; and for the subgroup of one DOSE/beagle immunization, the serum neutralizing antibody titers are 1:107.6, 1:90.5, 1:107.6, 1:152.2, and 1:128, respectively, and the virus challenge protection is 100%. For the dogs of control subgroup, no neutralizing antibody is detected with 5/5 of death. (2) Canine Parvovirus challenge group: for the subgroup of 0.01 DOSE/beagle immunization, the serum neutralizing antibody titers are 1:13.5, 1:26.9, 1:45.3, 1:53.8, and 1:32, respectively, and the virus challenge protection is 80%; for the subgroup of 0.1 DOSE/beagle immunization, the serum neutralizing antibody titers are 1:64, 1:90.5, 1:76.1, 1:64, and 1:32, respectively, and the virus challenge protection is 100%; and for the subgroup of one DOSE/beagle immunization, the serum neutralizing antibody titers are 1:90.5, 1:76.1, 1:90.5, 1:152.2, and 1:90.5, respectively, and the virus challenge protection is 100%. For the dogs of control subgroup, no neutralizing antibody is detected with 5/5 of death. (3) Canine Infectious Hepatitis virus challenge group: for the subgroup of 0.01 DOSE/beagle immunization, the serum neutralizing antibody titers are 1:6.72, 1:32, 1:16, 1:26.9, and 1:32, respectively, and the virus challenge protection is 80%; for the subgroup of 0.1 DOSE/beagle immunization, the serum neutralizing antibody titers are 1:76.1, 1:64, 1:53.8, 1:64, and 1:90.5, respectively, and the virus challenge protection is 100%; and for the subgroup of one DOSE/beagle immunization, the serum neutralizing antibody titers are 1:128, 1:90.5, 1:76.1, 1:107.6, and 1:152.2, respectively, and the virus challenge protection is 100%. For the beagles of control subgroup, no neutralizing antibody is detected with 5/5 of death. As can be seen, the triple live vaccine prepared in the present invention has excellent protective effects on preventing Canine Distemper, Canine Parvovirus Enteritis and Canine Infectious Hepatitis.

As can be known from technical common knowledge, the present invention can be achieved by other embodiments without separating the spiritual essence or essential features thereof. Therefore, in all aspects, all of the above disclosed embodiments are illustrated by examples, but not the only ones. All alterations in the scope of the present invention or equivalent to the scope of the present invention are included in the present invention.

What is claimed is:

1. A combination of vaccine strains comprising:

a Canine Distemper virus vaccine strain having a deposition accession number of CGMCC No. 19397;

a Canine Parvovirus vaccine strain having a deposition accession number of CGMCC No. 19398; and a Canine Infectious Hepatitis virus vaccine strain having a deposition accession number of CGMCC No. 19396.

2. A vaccine composition comprising the combination of claim 1.

3. The vaccine composition of claim 2, further comprising an excipient.

4. The vaccine composition of claim 3, wherein the vaccine composition is a live vaccine composition.

5. The vaccine composition of claim 3, wherein the ratio of the dosage of the Canine Distemper virus vaccine strain, the dosage of the Canine Parvovirus vaccine strains, the dosage of the Canine Infectious Hepatitis virus vaccine strains and the dry weight dosage of the excipient is $2\text{-}8\times10^{4.0}$ $TCID_{50}$:$0.5\text{-}3\times10^{5.0}TCID_{50}$:$-0.5\text{-}3\times10^{5.0}TCID_{50}$:-200-400 mg; and wherein, the $TCID_{50}$ of the Canine Distemper virus vaccine strain is obtained by calculating according to Reed-Muench method on the basis of Vero cell culture; the $TCID_{50}$ of the Canine Parvovirus vaccine strain is obtained by calculating according to Reed-Muench method on the basis of F81 cell culture; and the $TCID_{50}$ of the Canine Infectious Hepatitis virus vaccine strain is obtained by calculating according to Reed-Muench method on the basis of MDCK cell culture.

6. The vaccine composition of claim 3, wherein the excipient is an aqueous solution comprising 2-3 mg/mL polyvinyl pyrrolidone, 8-12 mg/mL sorbitol, 3-7 mg/mL glycine, 30-50 mg/mL sucrose, and 30-60 mg/mL trehalose.

7. A method for preparing the vaccine composition of claim 3, comprising mixing the combination of claim 1 and the excipient.

8. The method of claim 7, further comprising:

(i) respectively inoculating the vaccine strains in the combination of vaccine strains into culture cell to culture, to harvest crude viral liquids of the vaccine strains; specific to the Canine Distemper virus vaccine strain, the culture cell is Vero cell; specific to the Canine Parvovirus vaccine strain, the culture cell is F81 cell; and specific to the Canine Infectious Hepatitis virus vaccine strain, the culture cell is MDCK cell; and (ii) purifying the crude viral liquids of the vaccine strains to obtain purified viral liquids of the vaccine strains.

9. The method of claim 8, wherein specific to the Canine Distemper virus vaccine strain, a virus content in the purified viral liquid of vaccine strains is $\geq10^{5.0}TCID_{50}$/ml; specific to the Canine Parvovirus vaccine strain, a virus content in the purified viral liquid of vaccine strains is $\geq10^{6.0}TCID_{50}$/ml; and specific to the Canine Infectious Hepatitis virus vaccine strain, a virus content in the purified viral liquid of vaccine strains is $\geq10^{6.0}TCID_{50}$/ml.

10. The method of claim 7, further comprising drying the vaccine composition.

11. The method of claim 10, wherein the drying comprises:

(a) performing freezing on the vaccine composition to obtain a frozen vaccine composition;

(b) performing sublimation drying with temperature elevated by stages on the frozen vaccine composition under a vacuum condition to obtain a preliminarily dried vaccine composition; and (c) performing sublimation drying the preliminarily dried vaccine composition at a normal temperature under a vacuum condition to obtain the dried vaccine composition.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: F1a

<400> SEQUENCE: 1
gataaagcat gtcattatag tcctaa 26

<210> SEQ ID NO 2
<211> LENGTH: 19
<212> TYPE: DNA
<213> ORGANISM: Artificial Sequence
<220> FEATURE:
<223> OTHER INFORMATION: R1a

<400> SEQUENCE: 2
cttgagcttt cgacccttc 19

<210> SEQ ID NO 3
<211> LENGTH: 24
<212> TYPE: DNA
<213> ORGANISM: Artificial Sequence
<220> FEATURE:
<223> OTHER INFORMATION: F2a

<400> SEQUENCE: 3
atgctctcct accaagataa ggtg 24

<210> SEQ ID NO 4
<211> LENGTH: 25
<212> TYPE: DNA
<213> ORGANISM: Artificial Sequence
<220> FEATURE:
<223> OTHER INFORMATION: R2a

<400> SEQUENCE: 4
tcaaggtttt gaacggttac atgag 25

<210> SEQ ID NO 5
<211> LENGTH: 18
<212> TYPE: DNA
<213> ORGANISM: Artificial Sequence
<220> FEATURE:
<223> OTHER INFORMATION: P1b

<400> SEQUENCE: 5
ctcagccacc aactaaag 18

<210> SEQ ID NO 6
<211> LENGTH: 18
<212> TYPE: DNA
<213> ORGANISM: Artificial Sequence
<220> FEATURE:
<223> OTHER INFORMATION: P2b

<400> SEQUENCE: 6
gtaagcccaa tgctctat 18

<210> SEQ ID NO 7
<211> LENGTH: 24
<212> TYPE: DNA
<213> ORGANISM: Artificial Sequence -continued

```
<220> FEATURE:
<223> OTHER INFORMATION: P1c

<400> SEQUENCE: 7

cgcgctgaac attactacct tgtc                                          24


<210> SEQ ID NO 8
<211> LENGTH: 18
<212> TYPE: DNA
<213> ORGANISM: Artificial Sequence
<220> FEATURE:
<223> OTHER INFORMATION: P2c

<400> SEQUENCE: 8

cttcgtgtcc gcttcatg                                                 18
```